(12) United States Patent
Yirmiya

(10) Patent No.: US 10,626,178 B2
(45) Date of Patent: *Apr. 21, 2020

(54) TREATMENT OF MOOD AND STRESS RELATED DISORDERS

(71) Applicant: Raz Yirmiya, Jerusalem (IL)

(72) Inventor: Raz Yirmiya, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,596

(22) Filed: Mar. 23, 2018

(65) Prior Publication Data

US 2018/0230223 A1 Aug. 16, 2018

Related U.S. Application Data

(63) Continuation-in-part of application No. 14/913,453, filed as application No. PCT/IL2014/050747 on Aug. 20, 2014, now Pat. No. 9,950,036.

(60) Provisional application No. 61/868,273, filed on Aug. 21, 2013.

(51) Int. Cl.
| | | |
|---|---|---|
| *A61K 39/395* | (2006.01) | |
| *A61K 39/00* | (2006.01) | |
| *A61K 38/00* | (2006.01) | |
| *C07K 16/28* | (2006.01) | |
| *A61P 25/24* | (2006.01) | |

(52) U.S. Cl.
CPC .......... *C07K 16/2866* (2013.01); *A61P 25/24* (2018.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,407,481 A | 10/1983 | Bolton et al. |
| 4,819,834 A | 4/1989 | Thiel |
| 5,010,175 A | 4/1991 | Rutter et al. |
| 5,539,083 A | 7/1996 | Cook et al. |
| 6,960,648 B2 | 11/2005 | Bonny |
| 2002/0120100 A1 | 8/2002 | Bonny |
| 2003/0032594 A1 | 2/2003 | Bonny |

FOREIGN PATENT DOCUMENTS

| | | |
|---|---|---|
| WO | 9200091 A1 | 1/1992 |
| WO | 9211190 A2 | 7/1992 |
| WO | 9320242 A1 | 10/1993 |
| WO | 9709034 A1 | 3/1997 |

OTHER PUBLICATIONS

Bauer, J., et al. "Induction of cytokine synthesis and fever suppresses REM sleep and improves mood in patients with major depression", Biological Psychiatry, Nov. 1995, pp. 611-621, vol. 38 Issue 9 (11 pages).

Kreisel, T., et al., "Dynamic microglial alterations underlie stress-induced depressive-like behavior and suppressed neurogenesis", Molecular Psychiatry, Dec. 2014, pp. 699-709, vol. 19 Issue 6 (11 pages).

Steiner, J., et al. "Severe depression is associated with increased microglial quinolinic acid in subregions of the anterior cingulate gyrus: Evidence for an immune-modulated glutamatergic neurotransmission?", Journal of Neuroinflammation, 2011, vol. 8 Issue 94 (10 pages).

Olson, J., K., et al., "Microglia Initiate Central Nervous System Innate and Adaptive Immune Responses through Multiple TLRs", Journal of Immunology, Sep. 15, 2004, pp. 3916-3924, vol. 173, The American Association of Immunologists, Inc., Bethesda, MD, USA (10 pages).

Chen, C., et al., "Analogous Organic Synthesis of Small-Compound Libraries: Validation of Combinatorial Chemistry in Small-Molecule Synthesis", Journal of the American Chemical Society, 1994, pp. 2661-2662, vol. 116 (2 pages).

Koenig, et al., "C-Reactive Protein, a Sensitive Marker of Inflammation, Predicts Future Risk of Coronary Heart Disease in Initially Healthy Middle-Aged Men", Clinical Investigation and Reports, Jan. 19, 1999, vol. 99, Issue 2, pp. 237-242 (7 pages).

Lalancette-Herbert et al. "Selected Ablation of Proliferating Microgeal Cells Exacerbates Ischemic Injury in the Brain"; J. Neurosol. 2007, 27(1) : 2596-605 (10 pages).

*Primary Examiner* — Olga N Chernyshev
(74) *Attorney, Agent, or Firm* — The Roy Gross Law Firm, LLC; Roy Gross

(57) ABSTRACT

A pharmaceutical composition and method for treating or attenuating a mood or stress-related disorder in a subject having normal or low inflammatory state is provided. In some embodiments, the pharmaceutical composition and method of the invention comprise activating or stimulating microglia for treatment of mood or stress-related disorder.

3 Claims, 13 Drawing Sheets

Specification includes a Sequence Listing.

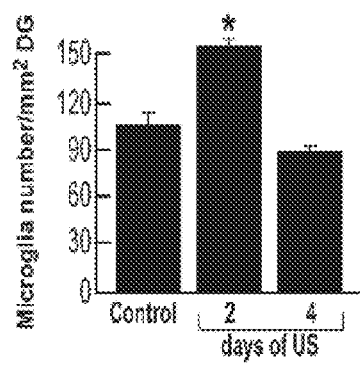
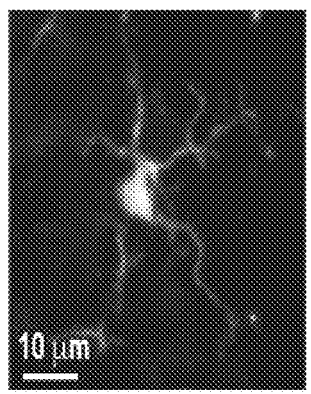
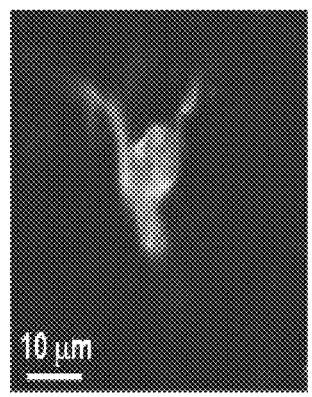
Figure 2a  Figure 2b  Figure 2c
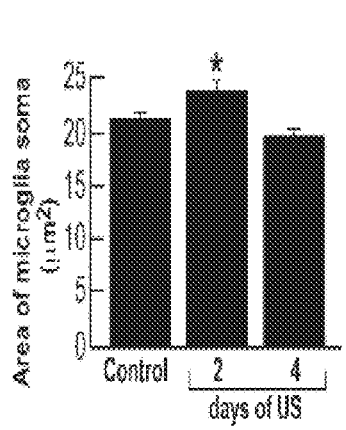
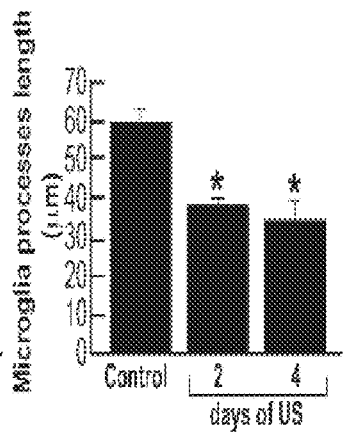
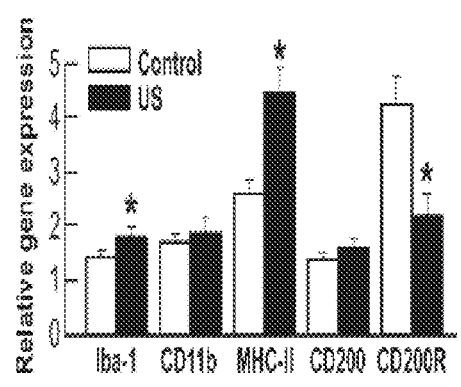
Figure 2d  Figure 2e  Figure 2f
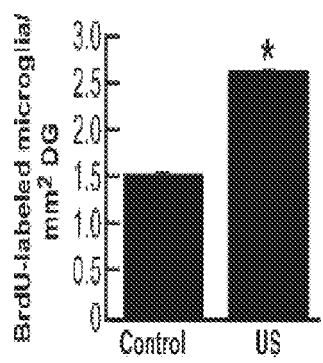
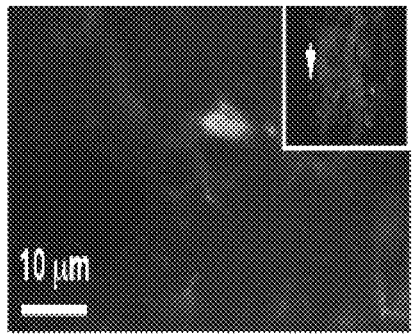
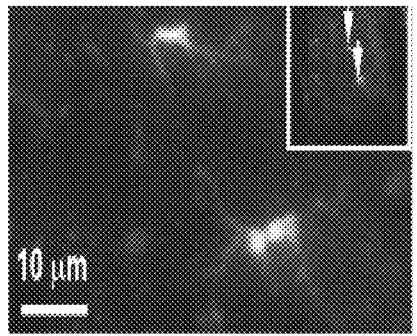
Figure 2g  Figure 2h  Figure 2i

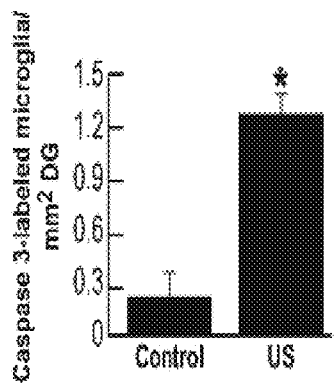
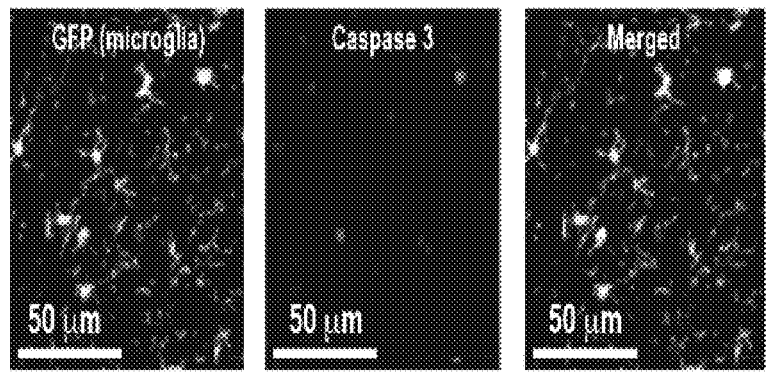
Figure 2j                Figure 2k
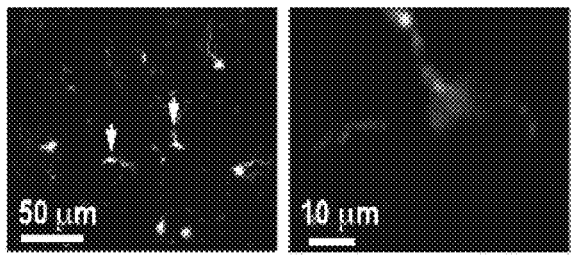
Figure 2l    Figure 2m
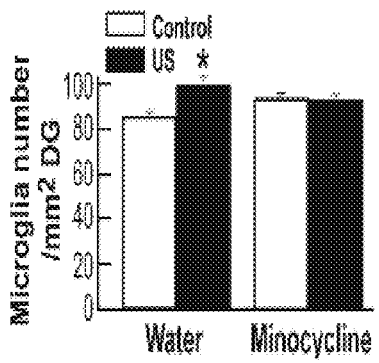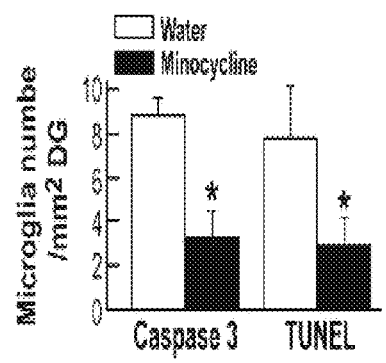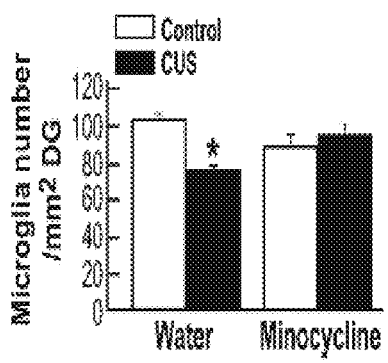
Figure 3a        Figure 3b        Figure 3c
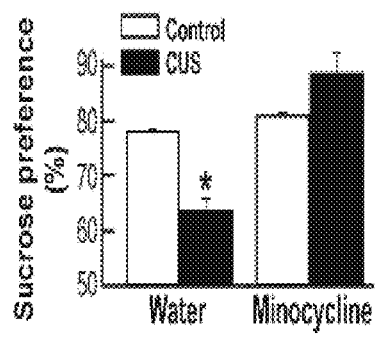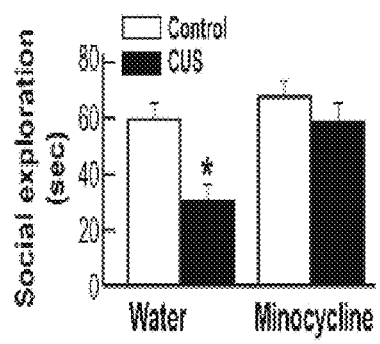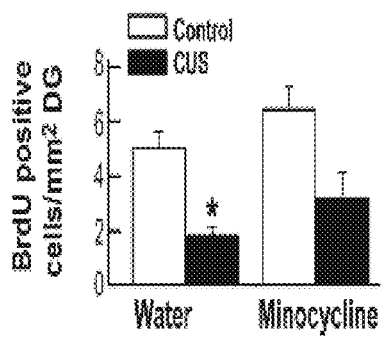
Figure 3d        Figure 3e        Figure 3f Figure 6d
Figure 6e
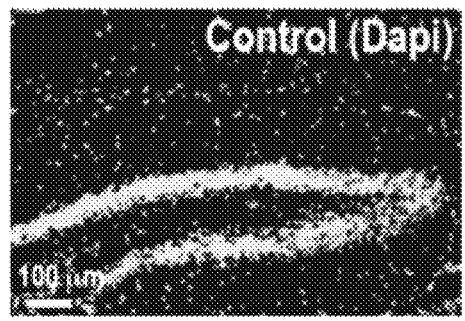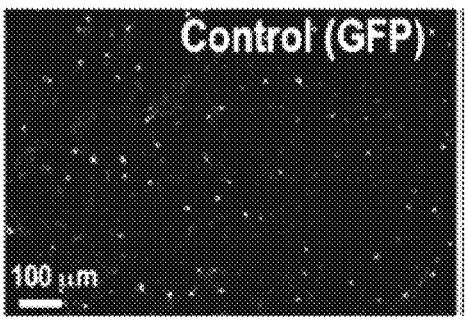
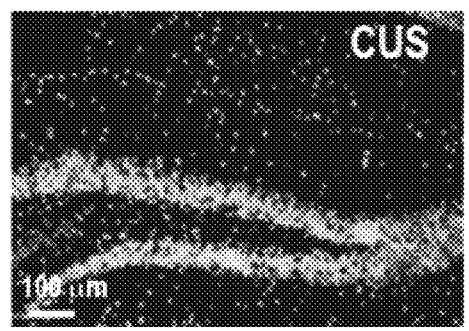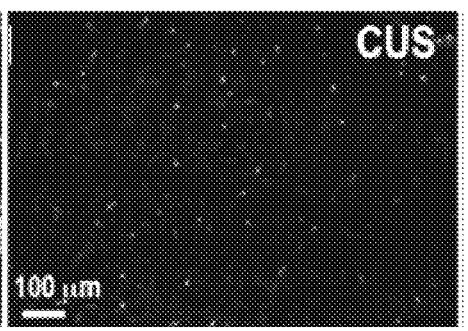
Figure 6f
Figure 6g
Figure 6h
Figure 6i
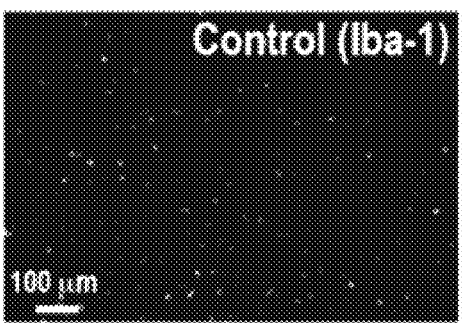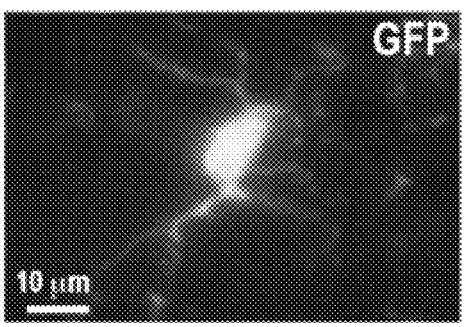
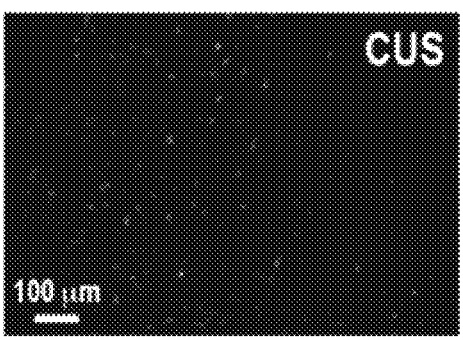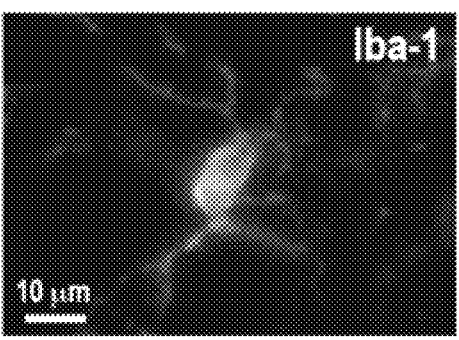
Figure 6j
Figure 6k Figure 7a
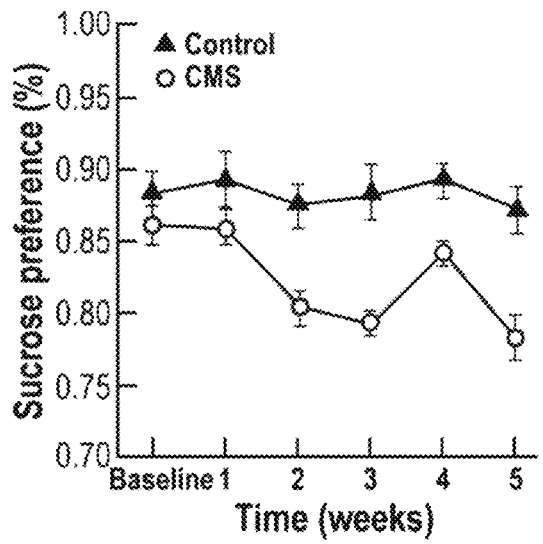
Figure 7b
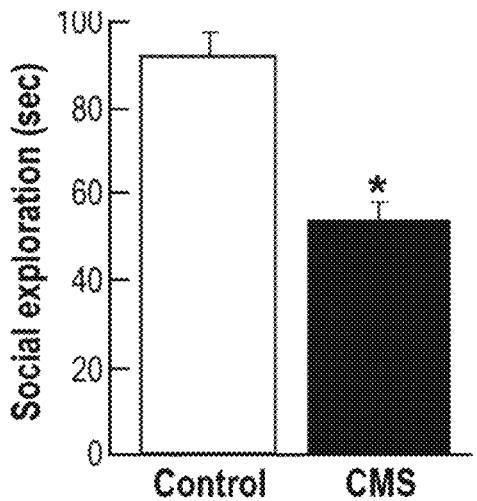
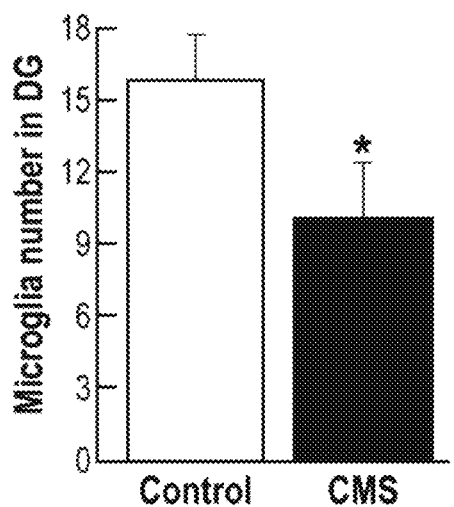
Figure 7c
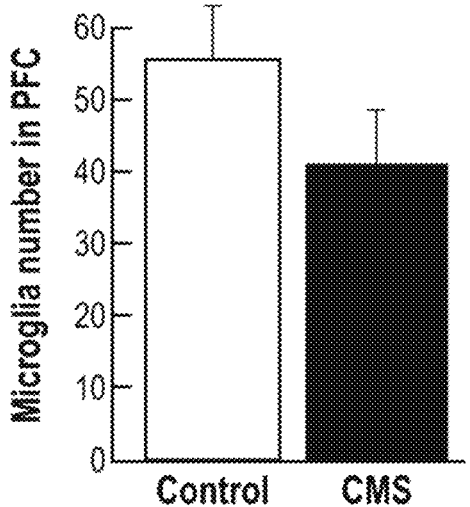
Figure 7d
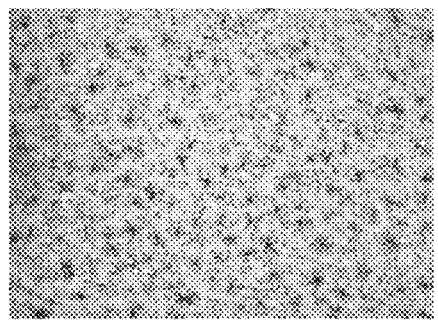
Figure 7e
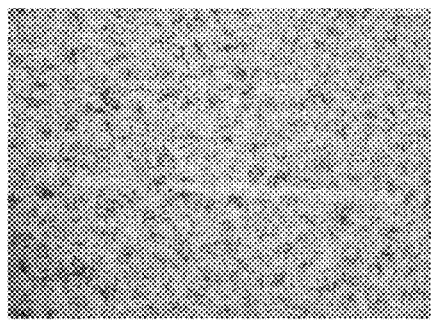
Figure 7f Figure 9a
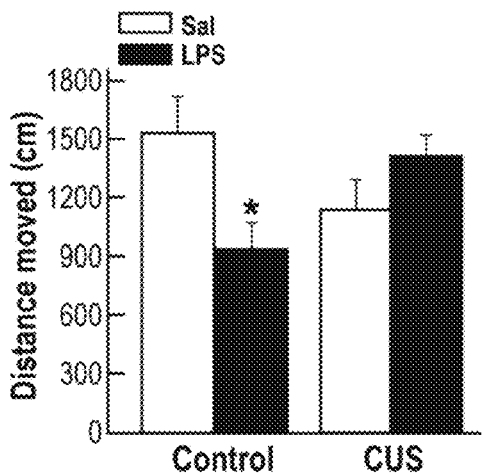
Figure 9b
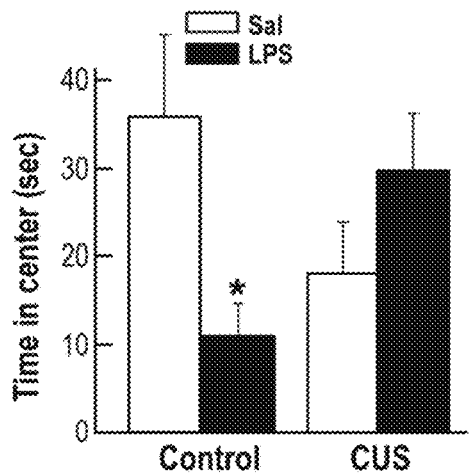
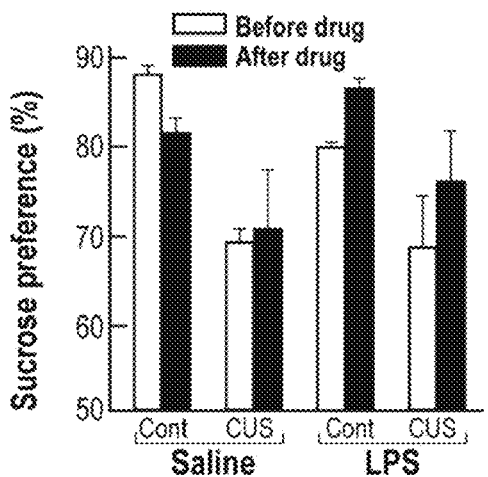
Figure 9c
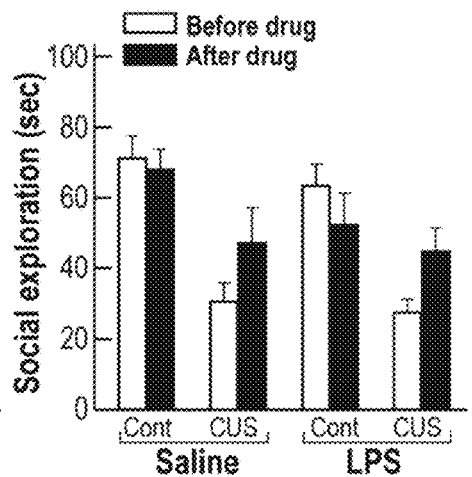
Figure 9d
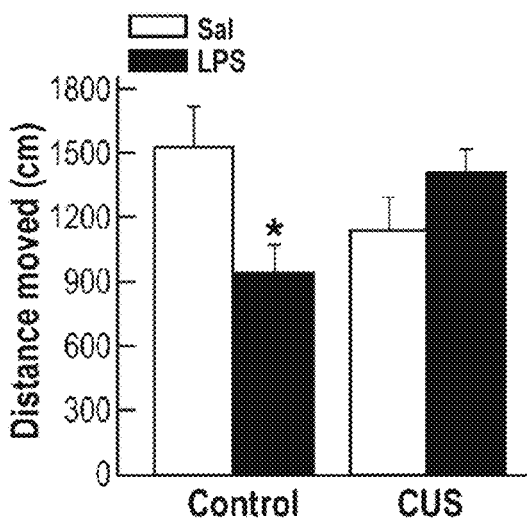
Figure 10a
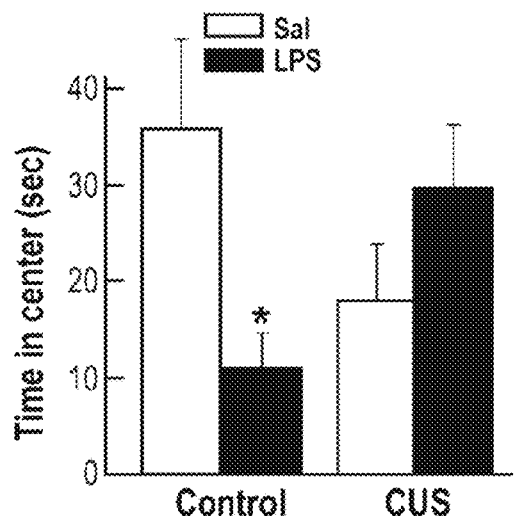
Figure 10b

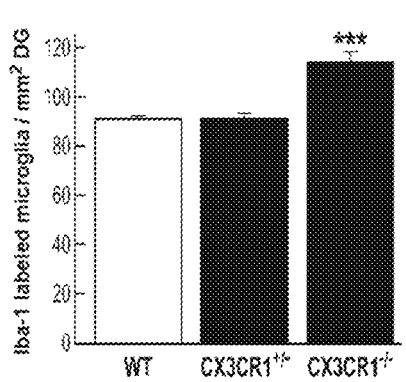
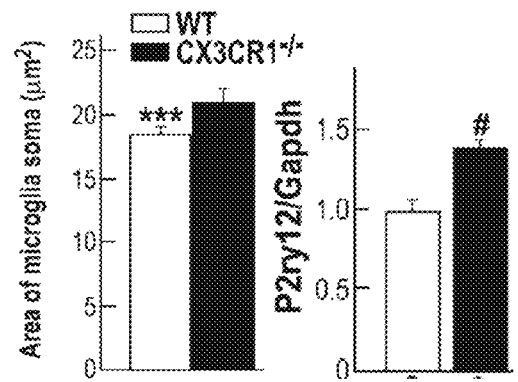
FIGURE 11a　　　FIGURE 11b　　FIGURE 11c
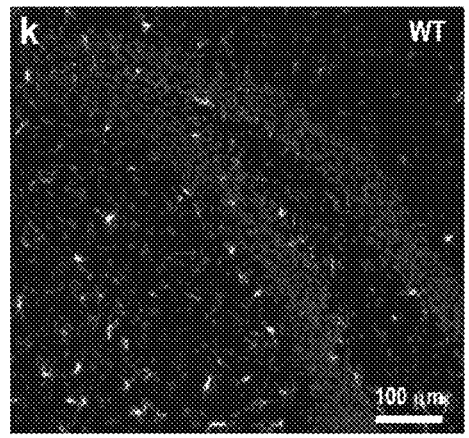
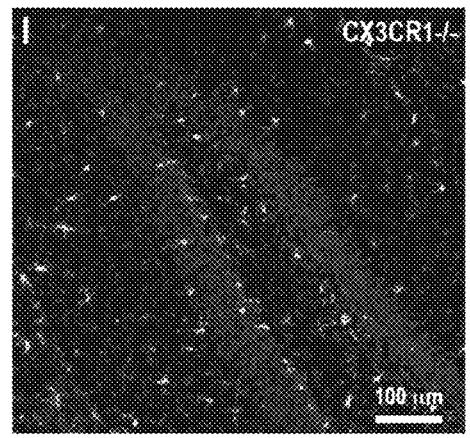
FIGURE 11d　　　　　　FIGURE 11e
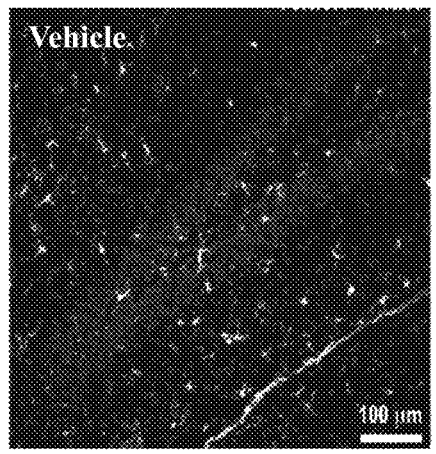
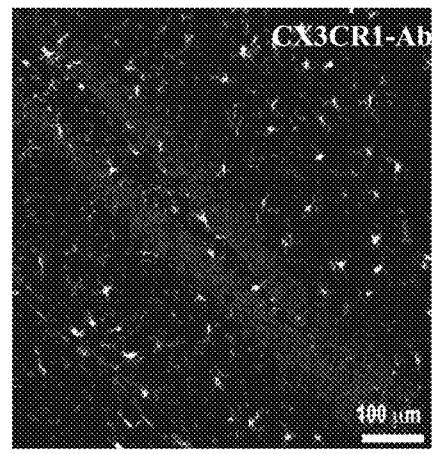
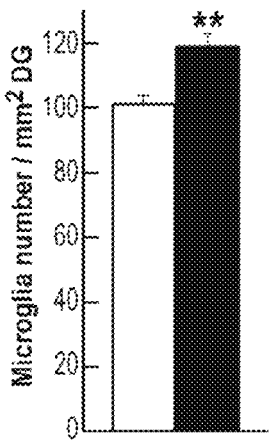
FIGURE 12a　　　　FIGURE 12b　　　　FIGURE 12c

TREATMENT OF MOOD AND STRESS RELATED DISORDERS

CROSS-REFERENCE TO RELATED APPLICATIONS

This application is a continuation-in-part of U.S. patent application Ser. No. 14/913,453 filed on Feb. 22, 2016 and titled "Treatment of Mood and Stress Related Disorders", now U.S. Pat. No. 9,950,036, which is a national phase of PCT Patent Application No. PCT/IL2014/050747 filed on Aug. 20, 2014, which claims the benefit of priority of U.S. Provisional Patent Application No. 61/868,273 filed on Aug. 21, 2013. The contents of the above applications are all incorporated by reference as if fully set forth herein in their entirety.

FIELD OF INVENTION

The present invention is directed to; inter alia, pharmaceutical compositions and methods for treating mood and stress related disorders.

BACKGROUND OF THE INVENTION

Despite impressive progress in understanding the molecular, cellular and circuit-level correlates of major depression, the biological mechanisms that causally underlie this disease are still unclear, hindering the development of effective preventive and therapeutic procedures. One possible reason for this situation is that almost all research in this area focuses on the involvement of abnormalities in neuronal functioning, whereas the involvement of non-neuronal brain cells was not thoroughly examined. Over the last decade it has been suggested that glia cells, particularly astrocytes, may be also involved in the pathophysiology of depression, however, almost no research has focused on the role of microglia in this disease.

Microglia, which comprise about 10% of brain cells, serve as the representatives of the immune system in the brain, and therefore their activation plays a major role in brain infection, injury, and neurodegenerative diseases. In addition, they are highly motile in their resting/quiescent state, and actively participate in synaptic changes, micro-damage repair, and neurogenesis.

Microglial activation and brain inflammatory cytokines have been implicated in the responsiveness to stress, which both in humans and in animal models has been implicated as a major trigger for depression. Specifically, exposure to acute stressful conditions can directly induce hippocampal microglial activation, and the microglial inhibitor minocycline was reported to block stress-induced hypothalamic IL-1 secretion. Furthermore, exposure to repeated restraint or social disruption stress for 4-14 days induced microglia proliferation and activation in several stress-responsive brain regions. In addition, the depressive and neurogenesis suppressive effects of chronic stress in rodents were found to be mediated by the microglial-derived cytokine interleukin-1. Together, these findings suggest that stress-induced microglial activation is critically involved in the development of depression and neurogenesis suppression. As such, the main hypothesis for treating stress and mood disorders proposes inhibiting microglial activation (e.g., Steiner et al., 2011, Journal of Neuroinflammation, 8:94).

Nevertheless, the art does not describe or suggest that following the initial phase of microglial proliferation and activation there is a subsequent phase of microglia apoptosis, dystrophy and decline, which contradictory to the art, should be treated by microglia stimulation.

There is an unmet need for improved compositions and methods for treating and/or ameliorating mood and stress related disorders.

SUMMARY OF THE INVENTION

The present invention relates to methods and compositions for treating a mood disorder or stress related disorder in a subject in need thereof. In some embodiments, there is provided use or administration of least one microglia activator or a combination of microglia activators for treatment of mood or stress related disorders.

According to one aspect, there is provided a method for treating or attenuating a major depressive disorder (MDD) in a subject having plasma C-reactive protein (CRP) levels lower than 3 mg/L, the method comprising administering to the subject a pharmaceutical composition comprising a therapeutically effective amount of a CX3C receptor 1 (CX3CR1) inhibitor and at least one pharmaceutically acceptable carrier or diluent.

In some embodiments, the method comprises a step of detecting an inflammatory state of said subject by determining the plasma level of at least one inflammatory marker selected from CRP, IL-6 and TNFα, wherein a level of any one of: (i) less than 3 mg/L CRP, (ii) less than 2.0 pg/ml IL-6, (iii) less than 3.8 pg/ml TNFα, and (iv) combination thereof, indicates the subject has an inflammatory state suitable for treatment by the CXC3R1 inhibitor.

In some embodiments, the method comprises a step of detecting an inflammatory state of said subject by determining Erythrocyte Sedimentation Rate (ESR), wherein an ESR level of less than 6.3 mm/h, indicates the subject has an inflammatory state suitable for treatment by the CX3CR1 inhibitor.

In some embodiments, a CX3CR1 inhibitor is an antagonist. In some embodiments, the antagonist is an antibody.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2a-2m. Effects of short-term US exposure on microglial status. (2a) Microglia number in the DG of mice exposed to no stress (Control), 2 days or 4 days of US ($F_{2,17}$=28.30, p<0.01; n=5/group). (2b) Representative pictures of CX3CR1-GFP labeled ramified microglia in a control mouse and (2c) activated microglia in a mouse exposed to 2 days of US. (2d) Effects of 2 or 4 days US exposure on microglial soma size and (2e) processes length ($F_{2,17}$=7.06 and 14.27, respectively, P<0.05). (2f) At 24 hr post US initiation in rats, hippocampal mRNA expression of Iba-1 and MHC-II was increased ($t_{10}$=−1.18 and −3.49, P<0.05 and P<0.01, respectively; n=6/group), whereas CD200R expression was decreased ($t_{10}$=3.34, P<0.01). (2g) Effects of 2 days US exposure on the number of proliferating DG microglia (double-labeled for GFP and BrdU) ($t_6$=−4.997, p<0.01; n=4/group). (2h) Representative pictures of proliferating DG microglia in control and (2i) 2 days US-exposed mice (green=GFP; red=BrdU; the inset depicts the location of these cells within the DG (Blue=Dapi)). (2j) Effects of 3 days US exposure on the number of activated/apoptotic microglia (doubled-labeled for GFP and caspase-3) ($t_6$=−5.48, p<0.0001; n=4/group). (2k) Representative pictures of BrdU (green) and caspase-3 (red) doubled-labeled microglia in the DG of a stressed mouse. (2l) TUNEL staining (red) in GFP-labeled DG microglia (green) from a mouse exposed to 4 days US. (2m) Higher magnification of an apoptotic microglia. *p<0.05 compared with the control group.

FIGS. 6a-6k. Neurobehavioral effects of CUS exposure. (6a) Effects of CUS exposure on sucrose preference and (6b) social exploration ($F_{1,26}=9.541$ and 18.00, p<0.05 and P<0.005, respectively; n=14/group). (6c) Effects of CUS on serum corticosterone levels ($t_{10}=2.099$ p=0.05). (6d) Representative pictures of the DG in a control mouse (stained with Dapi), as well as (6e) GFP-labeled and (6f) Iba-1-labeled microglia in this DG area. (6g) Representative pictures of the DG in a CUS-exposed mouse (stained with Dapi), as well as (6e) GFP-labeled and (6e) Iba-1-labeled microglia in this DG area. (6j) Representative picture of a normal GFP-labeled microglia cell, as compared with (6k) Iba-1 labeling of the same cell. *p<0.05 compared with all other groups.

FIGS. 7a-7f. Effects of CMS in rats on depressive-like symptoms and microglia number. Effects of CMS exposure on sucrose preference (7a; $F_{5,115}=3.62$, p<0.005) and (7b) social exploration ($F_{1,23}=28.67$, p<0.0001). (7c) Effects of CMS on the number of microglia/section of the DG ($t_9=1.93$, p<0.05; n=5-6/group) and (7d) the prelimbic cortex (p>0.1). (7e) Representative pictures of CD11b staining of microglia in control and (7f) CMS-exposed rats. *p<0.05 compared with the control group.

FIGS. 9a-9d. Effects of LPS on the behavioral effects of CUS. (9a) Effects of acute LPS administration on locomotor activity (distance moved) in the open filed test and (9b) the time spent in the center of the open field, in control and CUS-exposed mice ($F_{1,54}=5.018$ and 6.505, respectively, P<0.05, for stress by treatment interactions; n=15-16/group). (9c) Effects of acute LPS administration on sucrose preference and (9d) social exploration in control and CUS-exposed mice before drug (saline/LPS) injection (i.e., at the completion of the 5-weeks CUS exposure) and after drug treatment ($F_{1,29}=25.625$, P<0.0005 and $F_{1,28}=15.146$, P<0.001, respectively, for the overall stress effect, but no significance for the treatment or stress by treatment interactions). *p<0.05 compared with saline-injected control mice.

FIGS. 10a-10b. Anxiolytic effects of LPS in CUS-exposed ("depressed-like") mice. (10a) Effects of acute LPS administration on locomotor activity (distance moved) in the open field test and (10b) the time spent in the center of the open field, in control and CUS-exposed mice ($F_{1,54}=5.018$ and 6.505, respectively, P<0.05, for stress by treatment interactions; n=15-16/group). *p<0.05 compared with saline-injected control mice.

FIGS. 11a-11e. Genetic blockade of CX3CR1 signaling using mice with CX3CR1 knockout (CX3CR1$^{-/-}$ mice) increases microglial proliferation and activation. (11a) Microglial density (number of IBA-1-labeled microglia per mm$^2$) was significantly elevated in CX3CR1$^{-/-}$ mice, as compared with either WT or CX3CR1$^{-/-}$ mice. (11b) The average area of the microglial soma was significantly larger in CX3CR1$^{-/-}$ mice, as compared with control mice. (11c) The average level of mRNA expression of the microglial activation marker P2Y12 was significantly larger in CX3CR1$^{-/-}$ mice, as compared with WT mice. (11d) A representative picture, depicting IBA-1-labeled microglia (green) in the hippocampal DG of a WT mouse and (11e) a CX3CR1$^{-/-}$ mouse. The nuclei of all cells in the DG are stained with DAPI (blue).

FIGS. 12a-12c. Effects of CX3CR1 monoclonal antibody on hippocampal dentate gyms (DG) microglial number. (12a) Representative pictures of the hippocampal dentate gyms (DG) from a vehicle-treated control mouse and (12b) a CX3CR1 monoclonal antibody (CX3CR1-Ab)-treated mouse (middle panel). Iba-1-labeled microglia (green) are dispersed throughout the DG. The nuclei of all cells are stained with DAPI (blue). (12c) Two weeks of anti CX3CR1 monoclonal antibody (CX3CR1-Ab) significantly increased the microglial density (number/mm$^2$ DG) (p<0.05).

DETAILED DESCRIPTION OF THE INVENTION

The present invention relates to methods and compositions for treating a mood disorder or stress related disorder in a subject in need thereof.

Figure 5:
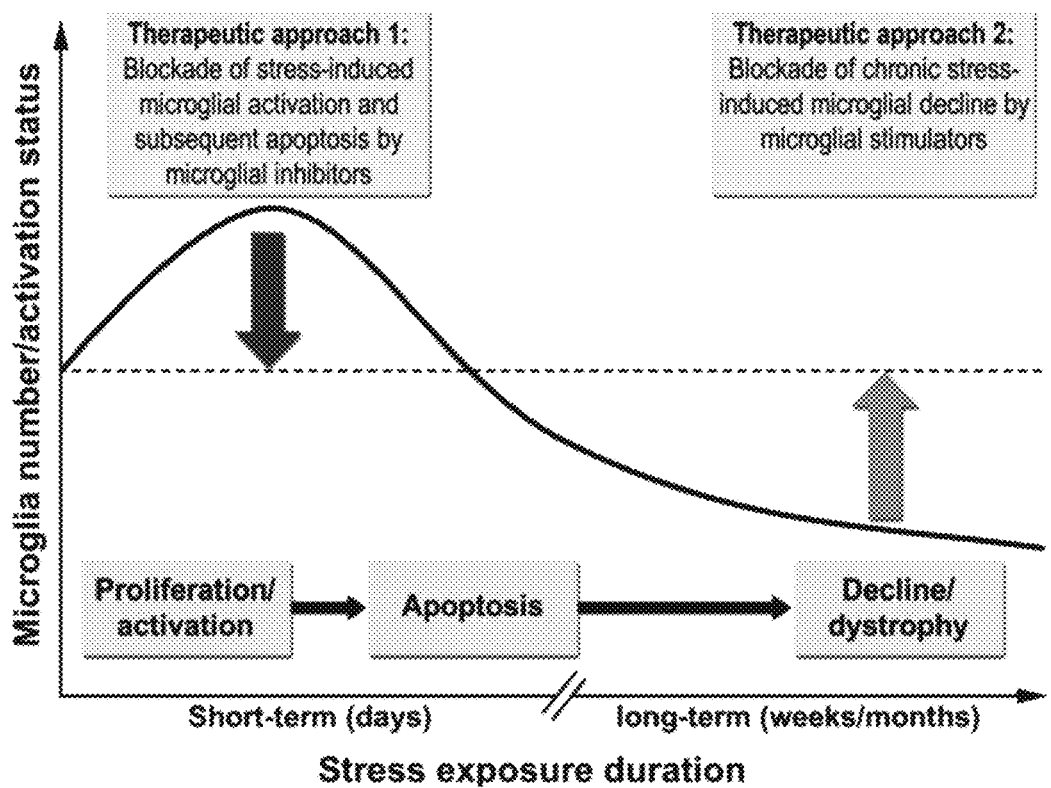
FIG. 5. A model representing the dynamic alterations in microglia status as a function of repeated stress exposure. An initial period of stress-induced IL-1-dependent microglial proliferation and activation leads to subsequent microglial apoptosis, decline in numbers, and assumption of dystrophic morphology, which are causally related to the development of depressive symptomatology and suppressed neurogenesis.

The present invention is based, in part, on the surprising finding that a specific patient population suffering from mood and depressive disorders can be treated by microglial activation. Without wishing to be bound by any mechanism of action, the invention demonstrates for the first time that chronic stress (CS) produces dynamic, bi-directional alterations in microglia status, including a known initial phase of proliferation and activation followed by a surprising microglia apoptosis, dystrophy and decline (FIG. 5). As exemplified hereinbelow, stimulation of microglia in CUS-exposed mice exhibiting suppressed microglia reversed the depressive-like neuro-behavioral symptomatology.

According to some embodiments, there is provided a method for treating or attenuating a mood or stress-related disorder in a subject in need thereof, the method comprising administering to the subject a pharmaceutical composition comprising a therapeutically effective amount of at least one microglia stimulator or an active variant, fragment or derivative thereof, and at least one pharmaceutically acceptable carrier or diluents. In some embodiments, said at least one microglia stimulator is selected from the group consisting of: CpG oligonucleotides, ATP, a-Crystallin (small heat shock protein), CX3CR1 antagonist, albumin, Monophosphoryl Lipid A (MPLA) and LPA, or an active variant, fragment or derivative thereof.

In one embodiment, there is provided a method for treating or attenuating a mood or stress-related disorder in a subject in need thereof, the method comprising administering to the subject a therapeutically effective amount of CpG oligonucleotides.

In another embodiment, there is provided a method for treating or attenuating a mood or stress-related disorder in a subject in need thereof, the method comprising administering to the subject a therapeutically effective amount of MPLA.

In another embodiment, there is provided a method for treating or attenuating a mood or stress-related disorder in a subject in need thereof, the method comprising administering to the subject a therapeutically effective amount of LPA.

In another embodiment, there is provided a method for treating or attenuating a mood or stress-related disorder in a subject in need thereof, the method comprising administering to the subject a therapeutically effective amount of ATP.

In another embodiment, there is provided a method for treating or attenuating a mood or stress-related disorder in a subject in need thereof, the method comprising administering to the subject a therapeutically effective amount of a-Crystallin.

In another embodiment, there is provided a method for treating or attenuating a mood or stress-related disorder in a subject in need thereof, the method comprising administering to the subject a therapeutically effective amount of an CX3CR1 inhibitor. In one embodiment, an inhibitor is an antagonist.

As defined herein, the term "a CX3CR1 inhibitor" refers to any molecule capable of preventing binding of the CXC3R1 receptor to its ligand (e.g., CX3CL1). In some embodiments, a CXC3R1 inhibitor is an antagonist. In some embodiments, CX3CR1 inhibitor is a small molecule. In some embodiments, CX3CR1 inhibitor is an antibody.

The term "antibody" is used in the broadest sense and specifically encompasses polyclonal and monoclonal antibodies and antibody fragments so long as they exhibit the desired biological activity. In some embodiments, the use of a chimeric antibody or a humanized antibody, derivative or fragment thereof, is also encompassed by the invention. In some embodiments, an antibody is a neutralizing antibody.

In some embodiments, an antibody derivative or fragment thereof comprises a portion of an intact antibody, comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs). In some embodiment, an antibody derivative or fragment thereof, includes a Fc.

In some embodiments, Fv is the minimum antibody fragment that contains a complete antigen-recognition and antigen-binding site. In some embodiments, a Fv derivative or fragment thereof, comprising only three hypervariable regions specific for an antigen, has the ability to recognize and bind antigen. In one embodiment, Fv has a higher binding affinity to an antigen compared to a Fv derivative or fragment thereof.

In some embodiments, the term "diabodies" refer to small antibody fragments with two antigen-binding sites.

In some embodiments, non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, neutralizing antibodies include: antibodies, fragments of antibodies, Fab and F(ab')2, single-domain antigen-binding recombinant fragments and nanobodies.

As would be apparent to one of ordinary skill in the art, CX3CR1 activity or signaling inhibition can be determined based on numerous methods, non-limiting examples of which include, cell migration assay of CX3CR1-positive cell to a cell expressing CX3CL1 or membrane-bound CX3CL1, chemotaxis assays in response to MIP-1α, MIP-1β and MCP-1, over-expression of the gene P2yr12 (e.g., by real-time RT-PCR), and others.

In another embodiment, there is provided a method for treating or attenuating a mood or stress-related disorder in a subject in need thereof, the method comprising administering to the subject a therapeutically effective amount of albumin.

In some embodiments, said subject is a subject having normal or low inflammatory state and said at least one microglia stimulator is a colony stimulating factor 1 receptor (CSF1R; also known as FMS and CD115) ligand (i.e., agonist). In another embodiment, said at least one microglia stimulator is selected from the group consisting of: macrophage colony-stimulating factor (M-CSF), granulocyte-macrophage colony-stimulating factor (GM-CSF) and IL-34 or an active variant, fragment or derivative thereof.

According to another embodiment, there is provided a method for treating or attenuating a mood or stress-related disorder in a subject in need thereof, the method comprising the steps of:
 (a) identifying, at least once, the inflammatory state of the subject; and
 (b) administering to a subject having a low or normal inflammatory state at least one microglia stimulator (e.g., M-CSF, GM-CSF and IL-34) or an active variant, fragment or derivative thereof.

According to another embodiment, there is provided a method for treating or attenuating a mood or stress-related disorder in a subject in need thereof, the method comprising the steps of:
 (a) identifying, at least once, the inflammatory state of the subject;
 (b) administering to a subject having an increased inflammatory state at least one microglia suppressive agent (e.g., minocycline, IL-1 signaling blockers); and
 (c) administering to a subject having a low or normal inflammatory state at least one microglia stimulator or an active variant, fragment or derivative thereof.

In another embodiment, said inflammatory state is detected by determining the level of activated microglia. In another embodiment, said inflammatory state is detected by determining the level of dystrophic microglia. In another embodiment, said low inflammatory state is an increase in dystrophic microglia.

In some embodiments, said normal or low inflammatory state is detected by determining the level of at least one inflammatory marker. In another embodiment, said inflammatory marker is CRP. CRP is a sensitive, nonspecific, acute-phase protein, produced in response to most forms of tissue injury, infection, and inflammation. CRP is produced by Kupffer cells in the liver, which are regulated by cytokines, such as IL-1, IL-6 and TNFα. Based on its stability, assay precision, accuracy, and availability; and the availability of standards for proper assay calibration, the high sensitivity CRP assay was recommended as the preferred inflammatory marker for coronary vascular disease. In normal humans, with no overt inflammatory condition, 95% of the population has CRP values<10 mg/L. In another study more than 50% of the normal population was found to have CRP levels lower than 2 mg/L (Koenig et al., 1999).

Several additional inflammatory markers can be also utilized for detection of a low inflammatory state, including IL-6 and TNFα. In some embodiments, there is provided treatment of a subject suffering from a mood or stress related disorder having IL-6 or TNFα levels lower than the levels of said cytokines in a control population (i.e., not having an inflammatory disease or disorder), typically less than 2.0 pg/ml for IL-6 and 3.8 pg/ml for TNFα. The Erythrocyte Sedimentation Rate (ESR) can also be used to define the inflammatory state. In some embodiments, there is provided treatment of a subject suffering from a mood or stress related disorder having less than 6.3 mm/h for ESR.

In another embodiment, said inflammatory state (e.g., levels of activated or dystrophic microglia) is assessed by positron emission tomography (PET) imaging. As known to one skilled in the art, microglia express the 18 kDa translocator protein (TSPO), which can be quantified by several PET ligands (Owen and Matthews, Int Rev Neurobiol. 2011; 101:19-39). The most common ligand is [(11)C]PK11195 (also termed peripheral benzodiazepine receptor), but newer ligands, such as [18F]-FEPPA, [11C]PBR28 and [18F]DPA are also available.

In some embodiments, the methods of the invention comprise assessing the inflammatory status of a subject at least twice, such as before and after treatment. In some embodiments, a subject is treated with a microglia activator of the invention when the microglia levels or activation rate are determined to be low or decreasing.

In another embodiment, said low inflammatory state is assessed by comparing the inflammatory state of said subject to a pre-determined inflammatory level. In another embodiment, said pre-determined inflammatory level is a pre-determined control level. In another embodiment, said pre-determined inflammatory level is an inflammatory level previously detected in said subject.

Microglia Activator

Microglial activation refers to the fact that when infection, injury or disease occur in the brain and affect nerve cells, microglia in the central nervous system become "active," causing inflammation in the brain, similar to the manner in which white blood cells act in the rest of the body. Under some conditions, microglia act like the monocyte phagocytic system. Activated microglia can generate large quantities of superoxide anions, with hydroxyl radicals, singlet oxygen species and hydrogen peroxide being a downstream product, any of which can be assayed in the preparations utilized in such methods of the invention.

Reactive microglia may be characterized by at least one of the following characteristics: 1) their cell bodies becoming larger, their processes becoming shorter and thicker, 2) an increase in the staining for several molecular activation markers, including Iba-1, Cd11b and ED-1, 3) proliferation and clustering, 4) production and secretion of inflammatory mediators, including pro-inflammatory (e.g., interleukin (IL)-1, IL-6 and tumor necrosis factor-α) and anti-inflammatory (e.g., IL-10, IL-1ra) cytokines, as well as additional inflammatory mediators (e.g., prostaglandins), 5) production and secretion of various neuroprotective factors, including brain-derived neurotrophic factor (BDNF) and insulin growth factor-1 (IGF-1), 6) production and secretion of chemo-attractive factors (chemokines), which recruit microglia from within the brain to specific brain locations and facilitate the infiltration of peripheral immune cells, for example, white blood cells, as compared to that found in the non-reactive state. In some embodiments micro glial activation is determined in at least one brain region or area, such as in the hippocampal dentate gyms (DG), in the prelimbic cortex or in any depression-related area.

The term "microglia activator" or "microglia stimulator" refers to a compound that may be nucleic acid-based molecule, amino acid-based molecule or a small organic molecule that causes activation of microglia as will be defined below. The activator may be an isolated full molecule, a fragment or a variant of the molecule as long as it causes microglia activation. The activator may cause the effect of microglia activation including but not limited to by acting directly on the microglia or by causing production, expression, secretion, of another agent effecting microglia activation.

In some embodiments, the microglia activator increases at least one of the following, all being indicative of microglia activation: increase in hippocampal microglia number as well as increase in number of proliferating microglia (as determined for example by microglia labeled with BrdU); reversal or decrease in dystrophic changes in microglia and increase their of cell body size and processes length; an increase of the expression of activation markers (including Iba-1, CD11b, and the inflammation-related enzyme caspase-1), and an increase in at least one neurotrophic factor such as BDNF and IGF-1.

Non-limiting examples of microglia activators to be used in the method and composition of the invention alone or in combination include but are not limited to: CX3CR1 antagonist, M-CSF, GM-CSF, IL-34 and other Fms-tyrosine-kinase-receptor ligands; interleukin (IL)-1β, IL-4; IL-6; IL-12/IL-23 p40 subunit; IL-27; Tumor necrosis factor-alpha (TNF-α), CD40 ligand (CD154), Interferon gamma (IFNγ), Monophosphoryl lipid A (MPL), Protollin, Amphotericin B (AmB) (e.g., Fungizone), polyinosinic-polycytidylic acid (poly (I:C), imiquimod, loxoribine, R-848, CpG oligonucleotides, 12-myristate 13-acetate (PMA), ATP, a-Crystallin, albumin, Lysophosphatidic acid (LPA), Endotheline, Platelet-activating factor (PAF), aluminum hydroxide (alum), MF59, and Adjuvant System 03 (AS03).

The term "macrophage colony stimulating factor receptor agonists", as used herein, relates to biologically active, recombinant, isolated peptides and proteins, including their biologically active fragments, peptidomimetics and small molecules that are capable of stimulating the Macrophage colony stimulating factor receptor, M-CSFR or c-fms.

Macrophage colony-stimulating factor (M-CSF) is 70- to 90-kD membrane bound disulfide-linked homodimer glycoprotein that stimulates proliferation and supports survival and differentiation of cells of the mononuclear phagocyte series. Three related cDNA clones of human M-CSF have been isolated, representing long (beta) intermediate (gamma) and short (alpha) splicing variants from the single M-CSF gene. In some embodiments, M-CSF has an amino acid sequence selected from SEQ ID NO: 1-3.

The M-CSF administered as part of the present invention may be a monomer or dimer. The dimer can be a homodimer composed of polypeptides having the above recited M-CSF reference amino acid sequences or a heterodimer composed of any two polypeptides having the above recited M-CSF reference amino acid sequences.

Granulocyte-macrophage colony stimulating factor (GM-CSF) is a well-known growth factor. The GM-CSF that can be employed in the inventive methods described herein are those full-length coding sequences, protein sequences, and the various functional variants, muteins, and mimetics that are known and available. The structure of both the coding DNA and protein are known as well as methods for recombinantly producing mammalian pluripotent granulocyte-macrophage colony-stimulating factor. Examples for different suitable forms and derivatives are sargramostim (LEUKINE®, PROKINE®), LEUCOTROPIN® or molgramostim (LEUCOMAX®). In some embodiments, GM-CSF comprises the amino acid sequence as set forth in SEQ ID NO: 4.

IL-34 is a cytokine that promotes the proliferation, survival and differentiation of monocytes and macrophages. IL-34 promotes the release of pro-inflammatory chemokines, and thereby plays an important role in innate immunity and in inflammatory processes. Signaling of IL-34 is via CSF1R and its downstream effectors stimulate phosphorylation of MAPK1/ERK2 AND MAPK3/ERK1. In some embodiments, IL-34 has an amino acid sequence as set forth in SEQ ID NO: 5.

In some embodiments, interleukin-1β has an amino acid sequence as set in NP_000567. In some embodiments, IL-4 has an amino acid sequence as set in NP_000580. In some embodiments, IL-6 has an amino acid sequence as set in NP_000591. In some embodiments, IL-12 has an amino acid sequence as set in UniProt accession no. P29459 or IL-23 p40 subunit (e.g., NP_000873). In some embodiments, IL-27 has an amino acid sequence as set in UniProt accession no. Q6P676.

In some embodiments, TNF-α has an amino acid sequence as set in NP_000585. In some embodiments, IFNγ has an amino acid sequence as set in NP_000610. In some embodiments, CD40 ligand (CD154) has an amino acid sequence as set in NP_000065.

In some embodiments, said microglia activator is at least one toll-like receptor agonist. Human microglia express all TLRs (1-9), and all agonists of these receptors can activate microglia (Olson and Miller, J Immunol. 2004 Sep. 15; 173.(6):3916-24). Activators of TLR3, TLR4, TLR 7/8 and TLR 9 have been found as strong microglial activators. As demonstrated hereinbelow, TLR4 agonist LPS produces anti-depressive effects, indicating that at least one of TLR1-9 agonists can be used as microglia-stimulating anti-depressants agent of the invention.

In some embodiments, said microglia activator is TLR3 agonists. Microglia express TLR3 and upon activation of this receptor exhibit marked activation, including cytokine production. In particular embodiments, said microglia activator is polyinosinic-polycytidylic acid (poly (I:C); CAS no. 24939-03-5), a synthetic double stranded RNA analog, found to activate microglia (i.e., induce an activated morphology and the production of inflammatory cytokines) through TLR3. Poly (I:C) may be particularly advantageous for the present invention since it can enter the brain, induce microglial activation and behavioral effects.

In some embodiments, said microglia activator is at least one CpG oligonucleotide (of classes A, B and C). CpG oligonucleotide are known in the art as short single-stranded synthetic DNA molecules that contain a cytosine triphosphate deoxynucleotide ("C") followed by a guaninetriphosphate deoxynucleotide ("G"). Bacterial DNA and synthetic oligodeoxynucleotides (ODN) containing unmethylated CpG motifs (CpG ODN) have been shown to stimulate the cells of the innate immune system through TLR-9. CpG ODN are currently used as vaccine adjuvants, including VaxImmune™ and PF-3512676. CpG ODN and other TLR9 agonists can activate microglia cells.

In some embodiments, said microglia activator is selected from TLR7 and TLR8 agonists, e.g., guanosine-based imidazoquinoline compounds including but not limited to imiquimod and loxoribine.

In some embodiments, said microglia activator is an adjuvant selected from MPL (e.g., CAS no. 1246298-63-4); protollin; Amphotericin B (AmB; e.g., CAS no. 1397-89-3) (FUNGIZONE™); aluminum hydroxide (alum; e.g., CAS no. 21645-51-2); MF59 or Adjuvant System 03 (AS03).

In some embodiments, said microglia activator is imiquimod (e.g., CAS no. 99011-02-6). In some embodiments, said microglia activator is loxoribine (e.g., CAS no. 121288-39-9). In some embodiments, said microglia activator is resiquimod (R-848; e.g., CAS no. 144875-48-9).

In some embodiments, said microglia activator is selected from Monophosphoryl lipid A (MPL; a chemically detoxified lipid A moiety derived from *Salmonella* Minnesota R595 LPS) or Lysophosphatidic acid (LPA).

In some embodiments, said microglia activator is a CX3C receptor type 1 (CX3CR1) antagonist. In some embodiments, said microglia activator is an antibody to the CX3CR1.

In some embodiments, said microglia activator is selected from 12-myristate 13-acetate (PMA) e.g., CAS no. 16561-29-8, ATP (e.g., CAS no. 56-56-5), a-Crystallin, albumin, Endotheline (e.g., UniProt accession no. P05305, P20800 or P14138) and platelet-activating factor (PAF; e.g., CAS no. 74389-68-7).

In another embodiment, the method further comprises administering to the subject a combination of pro-inflammatory cytokines (including, but not limited to, IL-1β, IL-6, IL-4, IL-6, IL-12/IL-23 p40 subunit, IL-27, TNF-α, IFN-γ), as well as cytokine inducers and other microglia stimulators including, but not limited to CpG oligonucleotides (of classes A, B and C), CD40 ligand (CD154), 12-myristate 13-acetate (PMA), ATP, a-Crystallin (small heat shock protein), albumin and Lysophosphatidic acid (LPA).

Included within the scope of the invention are polypeptides or polypeptide fragments being at least 70%, 75%, 80%, 85%, 90%, or 95% identical to the microglia activator described herein or fragments thereof.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides which have been identified and separated, fractionated, or partially or substantially purified by any suitable technique.

In the present invention, a "polypeptide fragment" refers to a short amino acid sequence of a larger polypeptide. Protein fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, about 100, about 200, and about 500 amino acids or more in length.

The terms "fragment," "variant," and "derivative" when referring to a polypeptide of the present invention include any polypeptide which retains at least some biological activity. Polypeptides as described herein may include fragment, variant, or derivative molecules without limitation, so long as the polypeptide still serves its function. Microglia activators (e.g., M-CSF) polypeptides and polypeptide fragments of the present invention may include proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. Polypeptides and polypeptide fragments of the present invention may comprise variant regions, including fragments as described above, and also polypeptides with altered amino acid sequences due to amino acid substitutions, deletions, or insertions.

Non-naturally occurring variants may be produced using art-known mutagenesis techniques. Polypeptides and polypeptide fragments of the invention may comprise conservative or non-conservative amino acid substitutions, deletions or additions and may also include derivative molecules. As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can contain the nucleotide sequence of the full-length cDNA sequence, including the untranslated 5' and 3' sequences, the coding sequences. A polynucleotide may comprise a conventional phosphodiester bond or a non-conventional bond (e.g., an amide bond, such as found in peptide nucleic acids (PNA)). The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. Polynucleotides may also contain one or more modified bases, DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, M-CSF contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or nucleic acid may be or may include a regulatory element such as a promoter, ribosome binding site, or a transcription terminator.

Pharmaceutical Use

According to some embodiments, the present invention provides a pharmaceutical composition for use in treating a mood or stress-related disorder in a subject having normal or low inflammatory state, the pharmaceutical composition comprising a therapeutically effective amount of at least one microglia stimulator selected from a CX3CR1-inhibitor M-CSF, GM-CSF and IL-34 or an active variant, fragment or derivative thereof, and at least one pharmaceutically acceptable carrier or diluent.

The term "pharmaceutical composition", as used herein, refers to at least one microglia stimulator with chemical components such as diluents or carriers that do not cause unacceptable adverse side effects and that do not prevent microglial stimulation.

As used herein, a "therapeutically effective amount" or "an amount effective" refers to an amount effective, at dosages and for periods of time necessary, to achieve the desired therapeutic result. A therapeutic result may be, e.g., lessening of symptoms, prolonged survival, improved mobility, improved social and vocational functioning, and the like. A therapeutic result need not be a "cure." A therapeutic result may also be prophylactic. Typically, since a prophylactic dose is used in subjects prior to or at an earlier stage of disease, the prophylactically effective amount will be less than the therapeutically effective amount.

The amount of the peptides of the present invention, which will be effective in the treatment of a particular disorder or condition will depend on the nature of the disorder or condition and on the particular peptide and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

In some embodiments, the microglia activator, for example, M-CSF is administered once per day, continuously or intermittently, such as until there is an improved in said mood or depressive symptomatology.

In some embodiments, the therapeutically effective amount of the microglia activator, for example, M-CSF is from between 0.1 and 100 µg/kg body weight per day. In some embodiments, the therapeutically effective amount is from between about 1 and 100 µg/kg body weight per day. In some embodiments, the therapeutically effective amount is from between 1 and 75 µg/kg body weight per day. In some embodiments, the therapeutically effective amount is from between 1 and 50 body weight per day. In some embodiments, the therapeutically effective amount is from between 1 and 40 µg/kg body weight per day. In some embodiments, the therapeutically effective amount is from between 1 and about 30 µg/kg body weight per day. In some embodiments, the therapeutically effective amount is from between 1 and 25 µg/kg body weight per day.

The term "treating" means an intervention performed with the intention of reversing or preventing the development or altering the pathology of, and thereby alleviating a disorder, disease or condition, including one or more symptoms of such disorder, disease, or condition. Preventing refers to prophylactic or preventative measures. The related term "treatment," as used herein, refers to the act of treating a disorder, symptom, disease or condition, as the term "treating" is defined above.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

The term "mood disorder" includes but is not limited to, depression of any type, including but not limited to unipolar major depressive episode, major depressive disorder, dysthymic disorder, treatment-resistant depression, bipolar depression, adjustment disorder with depressed mood, cyclothymic disorder, melancholic depression, psychotic depression, post-schizophrenic depression, depression due to a general medical condition, as well as to post-viral fatigue syndrome, and chronic fatigue syndrome.

In some embodiments, the invention includes treatment of a subject afflicted by schizophrenia, and particularly a schizophrenic subject characterized by low number and activity of microglia. In some embodiments, said subject is a schizophrenic subject afflicted by depression. In some embodiments said subject shows schizophrenic symptoms including but not limited to anhedonia and/or social problems/withdrawal. In some embodiments, the invention includes treatment of subtypes of schizophrenia, including but not limited to paranoid schizophrenia, disorganized schizophrenia, catatonic schizophrenia, undifferentiated schizophrenia, residual schizophrenia and simple schizophrenia.

The term "stress related disorder" includes but is not limited to stress-related disorders, including but not limited to Posttraumatic Stress Disorder, Acute Stress Disorder, Adjustment Disorder, Bereavement Related Disorder, Other Specified Trauma- or Stressor-Related Disorder and Unspecified Trauma, Generalized Anxiety Disorder, Anxiety Disorder due to general medical condition, and Anxiety disorder not otherwise specified.

Preferably the treatment is for improving at least one parameter related to depression and/or stress responsiveness, including depressed mood, anhedonia, decrease in appetite and significant weight loss, insomnia or hypersomnia, psychomotor retardation, fatigue or loss of energy, diminished ability to think or concentrate or indecisiveness, helplessness, hopefulness, recurrent thoughts of death, a suicide attempt or a specific plan for committing suicide, excessive anxiety, uncontrollable worry, restlessness or feeling keyed up or on edge, being easily fatigued, difficulty concentrating or mind going blank, irritability, sleep disturbance (difficulty falling or staying asleep, or restless unsatisfying sleep), sense of numbing, detachment, or absence of emotional responsiveness, a reduction in awareness of his or her surroundings, depersonalization, derealization, anxiety or increased arousal (e.g., difficulty sleeping, irritability, poor concentration, hypervigilance, exaggerated startle response, motor restlessness), avoidance of places and situations, distress or impairment in social, occupational, or other important areas of functioning.

The pharmaceutical compositions of the invention can be formulated in the form of a pharmaceutically acceptable salt of the peptides of the present invention or their analogs, or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, colloidal dispersions, emulsions (oil-in-water or water-in-oil), sprays, aerosol, ointment, tablets, pills, capsules, powders, gels, creams, ointments, foams, pastes, sustained-release formulations and the like. In particular embodiments, the pharmaceutical compositions of the present invention are formulated for aerosol administration for inhalation by a subject in need thereof.

In some embodiments, the composition of the invention is administered by intranasal or intraoral administration, using appropriate solutions, such as nasal solutions or sprays, aerosols or inhalants. Nasal solutions are usually aqueous solutions designed to be administered to the nasal passages in drops or sprays. Typically, nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal and oral preparations for inhalation, aerosols and sprays are known and include, for example, antibiotics and antihistamines and are used for asthma prophylaxis.

For intranasal or intraoral administration, the composition of the invention is provided in a solution suitable for expelling the pharmaceutical dose in the form of a spray, wherein a therapeutic quantity of the pharmaceutical composition is contained within a reservoir of an apparatus for nasal or intraoral administration. The apparatus may comprise a pump spray device in which the means for expelling a dose comprises a metering pump. Alternatively, the apparatus comprises a pressurized spray device, in which the means for expelling a dose comprises a metering valve and the pharmaceutical composition further comprises a conventional propellant. Suitable propellants include one or mixture of chlorofluorocarbons, such as dichlorodifluoromethane, trichlorofluoromethane, dichloro-tetrafluoroethane, hydrofluorocarbons, such as 1,1,1,2-tetrafluoroethane (HFC-134a) and 1,1,1,2,3,3,3-heptafluoropropane (HFC-227) or carbon dioxide. Suitable pressurized spray devices are well known in the art and include those disclosed in, inter alia, WO 92/11190, U.S. Pat. Nos. 4,819,834, 4,407,481 and WO 97/09034, when adapted for producing a nasal spray, rather than an aerosol for inhalation, or a sublingual spray. The contents of the aforementioned publications are incorporated by reference herein in their entirety. Suitable nasal pump spray devices include the VP50, VP70 and VP100 models available from Valois S.A. in Marly Le Roi, France and the 50, 70 and 100 µl nasal pump sprays available from Pfeiffer GmbH in Radolfzell, Germany, although other models and sizes can be employed. In the aforementioned embodiments, a pharmaceutical dose or dose unit in accordance with the invention can be present within the metering chamber of the metering pump or valve.

The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of a peptide of the invention, preferably in a substantially purified form, together with a suitable amount of carrier so as to provide the form for proper administration to the subject.

Microglial activators of the invention, polynucleotides encoding them, and compositions comprising them, can be delivered to a cell either through direct contact with the cell or via a carrier means. Carrier means for delivering microglial activators and compositions to cells are known in the art and include, for example, encapsulating the composition in a liposome moiety. Another means for delivery comprises attaching the microglial activator to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes.

The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

In some embodiments, the route of administration is improved by encapsulating the pharmaceutical agent in nanoparticles, such as to protect the encapsulated drug from biological and/or chemical degradation, and/or to facilitate transport to the brain thereby targeting microglia.

In another embodiment, the method further comprises administering to the subject vitamin E or a derivative thereof. As used herein, the term "vitamin E" includes alpha, beta, gamma, and delta-tocopherols and their derivatives, conjugates and metabolites. The vitamin E may also be a combination of alpha, beta, gamma, and delta-tocopherols. The alpha-form occurs naturally as the d-isomer known as d-alpha-tocopherol (d-2,5,7,8-tetramethyl-2-(4',8',12'-trimethyltridecyl)-6-chromanol). Other forms of vitamin E which can be used include: d-alpha-tocopheryl acetate, d-alpha-tocopheryl succinate, d-alpha-tocopheryl nicotinate and d-alpha-tocopheryl linoleate.

In another embodiment, the method further comprises administering to the subject at least one of the following anti-depressant drugs, including fluoxetine, sertraline, venlafaxine, citalopram, parocetine, trazodone, amitriptyline, nortriptyline, imipramine, dothiepin, lofepramine, doxepin, protriptyline, tranylcypromine, moclobemide, bupropion, nefazodone, mirtazapine, zolpidem, alprazolam, temazepam, diazepam, or buspirone.

Screening Methods

The present invention provides methods for treating or attenuating mood or depressive disorders, in some embodiments in subjects having low inflammatory state, using compounds that stimulate c-fms (macrophage colony stimulating factor receptor agonists or ligands). Macrophage colony stimulating factor receptor agonists stimulate the macrophage colony stimulating factor receptor, M-CSFR or also called c-fms, and may be biologically active, recombinant, isolated peptides and proteins, including their biologically active fragments, peptidomimetics or small molecules. In certain embodiments, such compounds are orally active and can cross the blood brain barrier.

Macrophage colony stimulating factor receptor agonists can be identified experimentally using a variety of in vitro and/or in vivo models. Isolated macrophage colony stimulating factor receptor agonists can be screened for binding to various sites of the purified macrophage colony stimulating factor receptor proteins. Compounds can be evaluated as potential factors for treatment of mood or depressive disorders using animal models (e.g., monkey, rat, or mouse models). Said candidate compounds may also be identified by known pharmacology, structure analysis, or rational drug design using computer-based modeling.

Candidate compounds and agents can be obtained from a wide variety of sources, including libraries of synthetic or natural compounds. For example, libraries of natural compounds in the form of bacterial, fungal, plant and animal extracts can be tested. Known pharmacological agents may be subjected to directed or random chemical modifications, e.g., alkylation, esterification, amidification, etc. to produce a library of structural analogs. Alternatively, a library of randomly or directed synthesized organic compounds or biomolecules (e.g., oligonucleotides and oligopeptides) can be used as a source of agents. Preparation and screening of combinatorial libraries are well known to those of skill in the art. See, e.g., U.S. Pat. No. 5,010,175, PCT Publication No. WO 93/20242, PCT Publication No. WO 92/00091, Chen et al., J. Amer. Chem. Soc. 116:2661 (1994), U.S. Pat. No. 5,539,083.

Candidate compounds may encompass numerous chemical classes, though typically they are organic molecules, preferably small organic compounds having a molecular weight of more than 50 and less than about 2,500 Daltons. They may comprise functional groups necessary for structural interaction with proteins (e.g., hydrogen bonding), and typically include at least an amine, carbonyl, hydroxyl, or carboxyl group. They often comprise cyclical carbon or heterocyclic structures and/or aromatic or polyaromatic structures substituted with one or more functional groups. They may be found among biomolecules including peptides, saccharides, fatty acids, steroids, purines, and pyrimidines, and structural analogs thereof.

In some embodiments, the present invention provides a method for the selection of a candidate compound or agent from a plurality of compounds, for treating a mood disorder or stress related disorder in a subject, the method comprising:

(a) contacting or treating microglia cell culture with a candidate compound;
(b) assessing the effects of the candidate compound on microglia number and/or proliferation status, and optionally on hippocampal neurogenesis status;
(c) selecting those candidates that increase microglia number and activation and preferably those that enhance hippocampal neurogenesis as well;
(d) validating the selected compounds of (c) in a behavioral model of mice, preferably mice that were exposed to chronic unpredictable stress (CUS); and
(e) selecting those compounds that were found to reduce the stress induced depressive-like behavioral changes.

In some embodiments, step (b) is performed using purified microglia cultures, derived from newborn CX3CR1-GFP (heterozygous or homozygous) mice or wild type (WT) mice to various concentrations of the candidate compound, or by administration of various doses of the candidate compound to CX3CR1-GFP or WT mice and assessing their effects on the number of hippocampal microglia.

Microglia status may be assessed by at least one of the following assays or a combination thereof: 1) Counting the number of hippocampal microglia, as well as proliferating microglia (i.e., microglia labeled with BrdU). It is expected that a suitable drug candidate will induce microglia proliferation and will reverse the CUS-induced reduction in hippocampal microglia number. 2) Assessing morphological changes in microglia, expecting that a suitable drug candidate will reverse the dystrophic changes in microglia and will increase their cell body size and processes length. 3) Assessing the expression of activation markers (including Iba-1, CD11b, and the inflammasome-related enzyme caspase-1), expecting that a suitable drug candidate will reverse the CUS-induced decrease in these markers. 4) Assessing the levels of neurotrophins, including BDNF and IGF-1, expecting that a suitable drug candidate will reverse the CUS-induced decrease in these markers. Typically, histological measures are compared with the corresponding results in saline-treated mice.

Neurogenesis may be assessed by daily administration of BrdU along with the putative anti-depressant drug. Following termination of the behavioral tests, the number of BrdU- and doublecortin-labeled cells in the hippocampus may be assessed using immunohistochemical methods well known in the art. It is expected that a suitable drug candidate will reverse the CUS-induced reduction in neurogenesis.

The behavioral assessment of step (d) may be measured in CUS-exposed (and control) subjects immediately before as well as after the compound administration.

Typically, the assessment may be carried out by exposing the mice for a period of 5 weeks (along with a control group of CUS-exposed mice administered with saline).

The assessment of the depressive behavior may be done for example by using at least one of the following tests:
1) Porsolt forced swim test (duration of floating and time to first float)
2) Anhedonia in the sucrose preference test
3) Level of social exploration/interest Selected compounds are those that show anti-depressive properties in this assessment set of tests (i.e., lower floating time, increased time to first float, higher sucrose preference and social exploration, as compared with their pre-drug condition and with respect to saline-injected controls).

In particular embodiments, a compound that will produce anti-depressive effects in the behavioral tests, reverse the CUS-induced reductions in hippocampal neurogenesis, increase the number of hippocampal microglia and will induce activated microglial morphology and elevated expression of activation markers will be considered a suitable candidate for clinical studies as "microglia-stimulating anti-depressant (MSAD)" drug.

It is to be noted that the term "a" or "an" entity, refers to one or more of that entity; for example, "a polypeptide," is understood to represent one or more polypeptides. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers.

As used herein, the term "consists of," or variations such as "consist of" or "consisting of," as used throughout the specification and claims, indicate the inclusion of any recited integer or group of integers, but that no additional integer or group of integers may be added to the specified method, structure or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Subjects were 2-4 months old male mice or rats. Animals were housed 2 (mice) or 3-4 (rats) per cage in temperature ($23\pm3°$ C.) controlled rooms with standard rodent chow and water available ad libitum (unless mentioned otherwise). The behavioral experiments were conducted during the first half of the dark phase of a reversed 12 hr light/dark cycle. All experiments were approved by the Hebrew University or the University of Colorado Committees for Animal Care and Use. Most experiments were conducted in heterozygous mice expressing transgenic enhanced green fluorescent protein (EGFP) in conjunction with the CX3C (fractalkine) receptor type 1 (CX3CR1), which in the brain is expressed exclusively by resident microglia along with their C57BL WT littermates. In experiments on the IL-1 system we used mice with transgenic overexpression of IL-1 receptor antagonist (IL-1raTG) under the control of the glial fibrillary acidic protein (GFAP) promoter and their C57BL/6×CBA WT controls. These mice were shown to secrete hIL-1ra only within their central nervous system and to be completely unresponsive to exogenous or endogenous IL-1β. In studies on rats we used adult male Sprague-Dawley rats (weighing 260-300 g at beginning of the experiment) (Harlan Laboratories).

Stress Exposure Paradigms

Subjects were exposed to chronic unpredictable stress (CUS), consisting of daily exposure to two stressors in a random order over a 5-week period. The effect of a shorter period of unpredictable stress was examined by exposing mice to various combinations of 2-3 of the same stressors over a period of 2 days. The list of CUS stressors included: cage shaking for 1 h with loud music and lights, on, lights on during the entire night (12 h), lights-off for 3 h during the daylight phase, flashing (stroboscopic) light for 6 h, placement in 4° C. cold room for 1 h, mild restraint (in small cages) for 2 h, 45° cage tilt for 14 h, wet cage for 14 h, exposure to fox, ferret, bobcat, or coyote smell for 2 h, noise in the room for 3 h, and water deprivation for 12 h during the dark period.

Behavioral Measurements

Sucrose Preference

Following baseline adaptation to sucrose for several days, animals were presented in the beginning of the dark circadian phase with two graduated drinking tubes, one containing tap water and the other 2% sucrose solution for 3 hr. Sucrose preference was calculated as the percent of sucrose consumption out of the total drinking volume.

Social Exploration

Each subject was placed in an observation cage and allowed to habituate to the cage for 15 min, following which a male juvenile was placed in the cage. Social exploration, defined as the time of near contact between the nose of the subject and the juvenile conspecific, was then recorded for three minutes, using computerized in-house software.

The Open Field Test

In the beginning of this test, each mouse was placed in the corner of a white 80×80 cm plastic arena with 50 cm-high walls. The time spent, and distance traveled in the center of the box (60 cm$^2$ area) vs. the outside zone (the rest of the box area) was measured over a three min period. Behavior was analyzed using EthoVision XT video tracking system and software (Noldus, The Netherlands).

The Porsolt Forced Swim Test

Mice were placed in 20 cm diameter glass cylinder filled to 10 cm with 21° C. water and their behavior was analyzed for five min. The time spent in immobility, defined as the absence of all movement except motions required to maintain the animal's head above the water, and the latency to first immobility episode were recorded using an in-house computerized software.

Pharmacological Treatments

The tricyclic antidepressant drug imipramine (Sigma, Israel) was administered via the drinking water at a dose of 20 mg/kg/day. LPS (from *Escherichia coli*, serotype 0111:B4, Sigma, Israel) was injected i.p. at a dose of 100 μg/kg. M-CSF (Prospect, Israel) was administered i.p. at a dose of 100 μg/kg.

Molecular and Biochemical Measurements

Real-Time RT-PCR

Total RNA was isolated from whole hippocampus utilizing a standard method of phenol:chloroform extraction. For detailed descriptions of RNA isolation, cDNA synthesis, and PCR amplification protocols refer to prior publication. cDNA sequences were obtained from Genbank at the National Center for Biotechnology Information (NCBI; www.ncbi.nlm.nih.gov). Primer sequences were designed using the Operon Oligo Analysis Tool (http://www.operon.com/technical/toolkit.aspx) and tested for sequence specificity using the Basic Local Alignment Search Tool at NCBI. Primers were obtained from Invitrogen. Primer specificity was verified by melt curve analyses. All primers were designed to span exon/exon boundaries and thus exclude amplification of genomic DNA. Primer sequences were as follows:

```
Iba-1, F:
                                          (SEQ ID NO: 6)
GGCAATGGAGATATCGATAT,

R:
                                          (SEQ ID NO: 7)
AGAATCATTCTCAAGATGGC;

CD11b, F:
                                          (SEQ ID NO: 8)
CTGGTACATCGAGACTTCTC,

R:
                                          (SEQ ID NO: 9)
TTGGTCTCTGTCTGAGCCTT;

MHCII, F:
                                          (SEQ ID NO: 10)
AGCACTGGGAGTTTGAAGAG,

R:
                                          (SEQ ID NO: 11)
AAGCCATCACCTCCTGGTAT;

CD200, F:
                                          (SEQ ID NO: 12)
TGTTCCGCTGATTGTTGGC,

R:
                                          (SEQ ID NO: 13)
ATGGACACATTACGGTTGCC;

CD200R, F:
                                          (SEQ ID NO: 14)
TAGAGGGGGTGACCAATTAT

R:
                                          (SEQ ID NO: 15)
TACATTTTCTGCAGCCACTG;

IL-Ib, F:
                                          (SEQ ID NO: 16)
CCTTGTGCAAGTGTCTGAAG,

R:
                                          (SEQ ID NO: 17)
GGGCTTGGAAGCAATCCTTA;

ICE, F:
                                          (SEQ ID NO: 18)
ATGCCGTGGAGAGAAACAAG,

R:
                                          (SEQ ID NO: 19)
CCAGGACACATTATCTGGTG;

IL-1RA, F:
                                          (SEQ ID NO: 20)
GTCTGGAGATGACACCAAG,

R:
                                          (SEQ ID NO: 21)
TCGGAGCGGATGAAGGTAA;

IL-IR1, F:
                                          (SEQ ID NO: 22)
ACCCAGTTCCTGACTTCAAG,

R:
                                          (SEQ ID NO: 23)
AGTCCCTGTACCAAAGCACT.
```

Primers were obtained from Invitrogen and their specificity was verified by melt curve analyses. All primers were designed to span exon/exon boundaries and thus exclude amplification of genomic DNA. PCR amplification of cDNA was performed using the Quantitect SYBR Green PCR Kit (Qiagen, Valencia, Calif.). Formation of PCR product was monitored in real time using the MyiQ Single-Color Real-Time PCR Detection System (BioRad, Hercules, Calif.). Relative gene expression was determined by taking the expression ratio of the gene of interest to β-Actin.

Corticosterone ELISA

To measure corticosterone levels, mice were killed by decapitation and trunk blood was collected. Samples were centrifuged for 15 min at 4° C. and the serum was removed. Levels of corticosterone were determined using ELISA Kit (Assaypro, USA).

Histological Measurements

Immunohistochemistry

Animals were perfused trans-cardially with cold PBS followed by 4% paraformaldehyde in 0.1 M PBS, and the brains were quickly removed and placed in 4% paraformaldehyde. After 24 h the brains were placed in 30% sucrose solution in PBS and then frozen in OCT.

BrdU immunofluorescent staining was performed on 8 μm frozen brain sections, fixated in 50% formamide/2×SCC (0.3M NaCl and 0.03 M sodium citrate) for 2 hours at 65° C. After one wash with 2×SCC, sections were incubated in 2 N HCl for 30 minutes at 37° C. Sections were then rinsed in 0.1 M boric acid at pH 8.5 and washed 3 times in PBS, following which they were incubated in 3% normal goat serum in 1% BSA/0.1% Triton for 30 min at room temperature and then incubated with rat monoclonal anti-BrdU antibody (1:200, AbD serotec) for 48 hours at 4° C. Sections were then incubated with a secondary antibody (1:200 goat anti rat IgG, conjugated to Alexa 555, Invitrogene) for 2 hours at room temperature and counter-stained with DAPI (Sigma, Israel).

In some experiments microglia were visualized using an antibody to the microglia activation marker ionized calcium-binding adapter molecule-1 (Iba-1). Brain sections were first fixed in 2% paraformaldehyde, and after 3 PBS washes they were incubated over-night in 3% normal goat serum in 5% BSA with the primary antibody (rabbit anti Iba-1 1:220, Wako, Japan) at 4° C. Sections were then incubated with the secondary antibody (goat anti rabbit, 1:200; Invitrogen) for 1 hour at RT and counter-stained with DAPI (Sigma, Israel).

In rats, microglia were visualized with an antibody that recognizes the cluster of differentiation molecule 11B (CD11b), a microglia surface marker in brain. CD11b staining was conducted using the avidin-biotin-horseradish peroxidase (ABC) reaction. Briefly, sections were washed 3 times in PBS followed by incubation in a 0.3% hydrogen peroxide solution. Sections were then incubated with mouse monoclonal antisera against CD11b (1:100; BD Pharmingen, United States) overnight at 4° C. The following day tissue was incubated in biotinylated goat α-mouse IgG secondary antibody (1:200; Jackson ImmunoResearch, United States) at RT. Slices were next incubated in ABC (Vectastain Elite ABC kit, Vector Labs, United States) in PBS for 1 hour at RT. Next, sections were washed in phosphate buffer (without saline), and then exposed to a solution containing 3,3'-diaminobenzidine (DAB), cobalt chloride, nickel ammonium sulfate, ammonium chloride, and glucose oxidase in phosphate buffer. The peroxidase reaction was initiated by the addition of a glucose solution and reacted with the tissue for approximately 10 minutes. The reaction was terminated by washing sections in PBS. Stained tissue sections were dehydrated in a series of alcohols and defatted with Histoclear. Slides were then cover-slipped with Permount.

Caspase 3 immunofluorescent staining was performed on 50 μm frozen floating brain sections. The sections were fixed in methanol, washed 3 times with PBS and incubated over-night in 3% normal goat serum in 5% BSA with the primary antibody (rabbit anti Caspase-3 1:200, Cell signaling Technologies, Beverly, Mass., USA) at 4° C. Sections were then incubated with the secondary antibody (goat anti rabbit cy3, 1:200; Jeckson) for 1 hour at RT and counter-stained with DAPI (Sigma, Israel).

Apoptosis was detected and quantified using a commercially available fluorescent terminal deoxynucleotidyl transferase nick-end labeling (TUNEL) kit, according to the manufacturer's protocol (Roche Diagnostics Corporation, Indianapolis, Ind., USA). For positive control, sections were incubated with recombinant DNase I (Roche Diagnostics Corporation, Indianapolis, Ind., USA).

Image Analysis

Images were captured using Nikon Eclipse fluorescent microscope and CI Nikon confocal microscope and camera. The number of GFP-labeled microglia (and in some studies the number of BrdU-labeled microglia and other cells), as well and the microglial soma area were automatically measured at ×10 magnification in a defined area exclusively containing the entire Dentate Gyrus or prelimbic cortex, for each slide, using Nikon Imaging Elements Software (NIS-Elements). Microglia processes length was measured by capturing images at 40× magnification and by manual tracing of the processes of 4 randomly selected cells/section their processes using the NIS Elements software.

Statistical Analysis

All data are presented as mean±SEM. All statistical comparisons were computed using SPSS 19.0 software and consisted of t-tests, one-way, two-way or three-way analyses of variance (ANOVAs) followed by Tukey post hoc analyses, when appropriate.

CX3CR1 Analysis

Subjects

Subjects were 2-3 months old male CX3CR1-GFP transgenic mice (on C57BL/6 genetic background) and their wild type (WT) controls. The GFP gene was knocked-in under the CX3CR1 promoter. The inventors had used homozygous CX3CR1-GFP mice, with CX3CR1 deficiency (CX3CR1$^{-/-}$), as well as heterozygous CX3CR1-GFP mice, which express both the functional CX3CR1 gene and GFP (CX3CR1$^{-/-}$ mice) and wild-type (WT) mice as controls. Animals were housed in air-conditioned rooms (23° C.), with food and water ad libitum, and were kept in a reversed light/dark cycle, with lights off from 8 a.m. to 8 p.m. All the experiments were approved by the Hebrew University Ethics Committee on Animal Care and Use.

Administration of CX3CR1 Blocking Antibodies

Adult WT mice were anesthetized with Isoflurane (Terrell, USA) and placed in a stereotaxic apparatus. A burr hole was drilled posterior to bregma, using the following formula: [−0.4−0.66×(bl−3.8)] mm (bl=distance between bregma and lambda), 1.5 mm lateral to the midline, and a 30-gauge brain-infusion cannula (Alzet, Calif., USA) was lowered 2.2 mm below the skull surface into the right lateral ventricle. The guide cannula was secured to the skull with three stainless-steel screws and dental cement. An osmotic minipump (Alzet., Calif., USA) was implanted subcutaneously and attached with catheter tubing to the cannula. The minipumps delivered artificial CSF for 7 days, while allowing the animals to recover from the procedure. On day 7 post implantation, the minipumps were exchanged with new ones filled with CX3CR1 blocking antibody (Torrey pines bio labs, NJ, USA; 6 μg per day) or artificial CSF (vehicle) for 14 additional days. Mice were sacrificed after 14 days of the antibody delivery.

Stress Exposure Paradigms

Subjects were exposed to chronic unpredictable stress (CUS), consisting of daily exposure to two stressors in a random order over a 5-week period. The effect of a shorter period of unpredictable stress was examined by exposing mice to various combinations of 2-3 of the same stressors over a period of 2 days. The list of CUS stressors included: cage shaking for 1 h with loud music and lights on, lights on during the entire night (12 h), lights-off for 3 h during the daylight phase, flashing (stroboscopic) light for 6 h, placement in 4° C. cold room for 1 h, mild restraint (in small cages) for 2 h, 45° cage tilt for 14 h, wet cage for 14 h, exposure to fox, ferret, bobcat, or coyote smell for 2 h, noise in the room for 3 h, and water deprivation for 12 h during the dark period.

Sucrose Preference

Following baseline adaptation to sucrose for 3-4 days, mice were presented in the beginning of the dark circadian phase with two graduated drinking tubes, one containing tap water and the other 1% sucrose solution for 4 h. Sucrose preference was calculated as the percentage of sucrose consumption out of the total drinking volume.

The Object Recognition Test

Mice were habituated to the test cages for three consecutive days (during 1 h, 5 min, and 5 min exposure periods, respectively). On the fourth day, mice were allowed to explore two identical objects until they reached a criterion (a total of 20 s nose-directed exploration of the objects) or for 3 min. Mice who failed to explore the objects for at least 10 s were discarded from the experiment. Twenty-four hours later, mice were allowed to explore one old and one new object. Nose-directed exploration time for each of these objects was recorded until the criterion was reached or for 3 min total.

Immunohistochemistry

After termination of the enrichment protocols and behavioral testing, animals were perfused trans-cardially with cold phosphate buffer solution (PBS), followed by 4% paraformaldehyde in 0.1 M PBS, and the brains were quickly removed and placed in 4% paraformaldehyde. After 24 h, the brains were placed in 30% sucrose solution in PBS for 48 h and then frozen in OCT. Coronal sections (8 μm) were serially cut along the rostro-caudal axis of the olfactory bulbs and the dorsal hippocampus using a cryostat (Leica) and mounted on slides.

To determine microglial Iba-1 expression, sections were fixed with 2% PFA, followed by blocking with 3% NGS in 5% BSA. The primary antibody, rabbit anti iba-1 (1:200, Wako) was added for 24 h in 4° C. The secondary antibody, goat anti rabbit IgG (Molecular Probes), was added for 1 h at RT. For assessment of MHC-II expression, sections were incubated in a solution of 0.1% Triton-X100 in PBS for 1 hr, followed by incubation with the primary antibody (mouse anti MHC-II 1:50, Millipore, Chemicon), diluted in 0.1% triton X-100 for 24 h in 4° C. Sections were then incubated with the secondary antibody (goat anti mouse IgG conjugated to Alexa 555) for 1 hr in RT. All slides were counterstained with DAPI.

Estimation of Microglial Number and Soma Area

Images were captured using Nikon Eclipse microscope and camera, at 10× and 40× magnifications. In each slide the number of GFP-labeled microglia (that were also counterstained with DAPI to ascertain nuclear staining) as well as the microglial soma area were automatically measured in a defined area exclusively containing the entire hippocampal dentate gyrus, using Nikon Imaging Elements Software (NIS-Elements). These measurements were conducted by an experimenter who was blind with respect to the group assignment of the animals. For each brain, microglia number and morphology were assessed in 16 sections along the entire rostro-caudal axis of the dorsal hippocampus, and the number of microglia and their soma areas were averaged.

Real-Time Quantitative PCR

Mice were sacrificed by decapitation. Each brain was quickly removed on an ice-cold glass plate, and the hippocampus was dissected out under a binocular, tissues were weighed, flash frozen in liquid nitrogen, and stored in –80° C. until RNA extraction. RNA was extracted using PerfectPure RNA extraction kit (5 PRIME, Darmstadt, Germany) and RNA samples (2 μg) were reverse transcribed using the QuantiTect Reverse Transcription Kit from Qiagen (Hilden, Germany) including DNase treatment of contaminating genomic DNA. Expression of mRNA was determined by qPCR, using glyceraldehyde-3-phosphate dehydrogenase (Gapdh) as a normalizing gene. Primers were designed using PrimerQuest IDT (Integrated DNA Technologies, Inc, San Diego, Calif., USA). The following primers were used:

Gapdh, F:
(SEQ ID NO: 24)
TCTCCCTCACAATTTCC,

R:
(SEQ ID NO: 25)
GGGTGCAGCGAACTTT;

P2yr12 F:
(SEQ ID NO: 26)
CTGGGACAAACAAGAAGAAAGG,

R:
(SEQ ID NO: 27)
CCTTGGAGCAGTCTGGATATT.

Statistical Analysis

All data are presented as mean±SEM. All statistical comparisons were computed using SPSS 19.0 software and consisted of t-tests, one-way, two-way or three-way analyses of variance (ANOVAs) followed by Tukey post hoc analyses, when appropriate.

Example 1

Figure 1A:
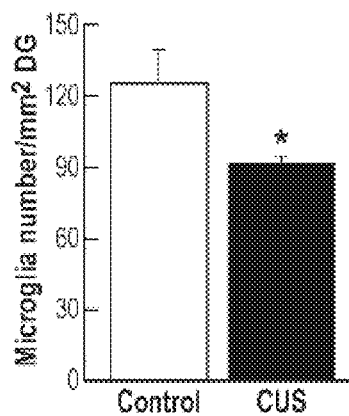
FIGS. 1a-1j. Effects of CUS exposure on microglia number, morphology and functioning. (1a) Effects of CUS exposure on the number of microglia in the dentate gyrus (DG) ($t_6$=2.53, P<0.05; n=4/group). (1b) Representative picture of CX3CR1-GFP labeled microglia in the DG of control and (1c) CUS-exposed mice. (1d) Effects of CUS exposure on the number of microglia in the medial prefrontal cortex (PFC) (p>0.1), and (1e) the somatosensory cortex (p>0.1). (1f) Representative pictures of a ramified microglial cell in the DG of a control mouse and (1g) a dystrophic microglial cell in the DG of CUS-exposed mouse. (1h) Effects of CUS exposure on the length of microglial processes ($t_6$=2.66, P<0.05) and (1i) the area of their soma ($t_6$=2.01, P<0.05). (1j) Effects of CMS in rats on the mRNA expression levels of Iba-1, CD11b and CD200 ($t_9$=2.21, 2.34, and 4.13, respectively, p<0.05), as well as MHC-II and CD200 receptor (CD200R). *p<0.05 compared with control untreated animals.
Figure 1B:
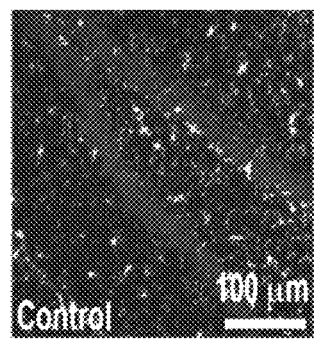
Figure 1C:
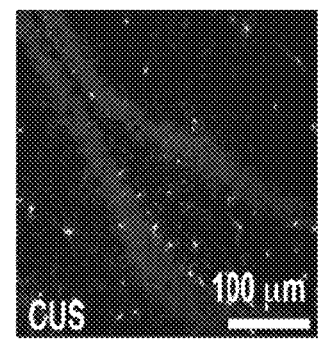
Figure 1D:
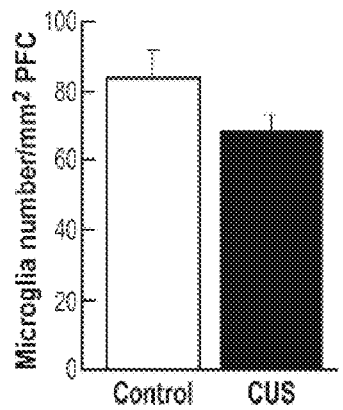
Figure 1E:
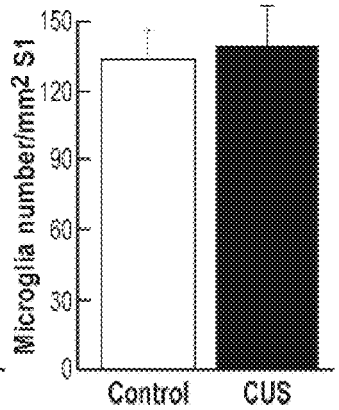
Figure 1F:
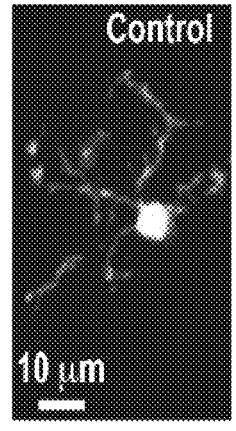
Figure 1G:
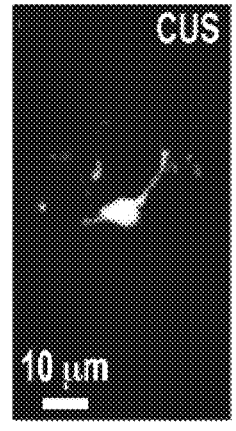
Figure 1H:
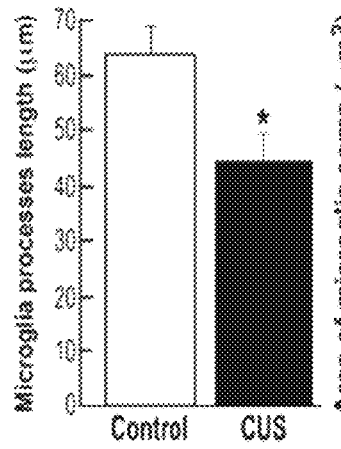
Figure 1I:
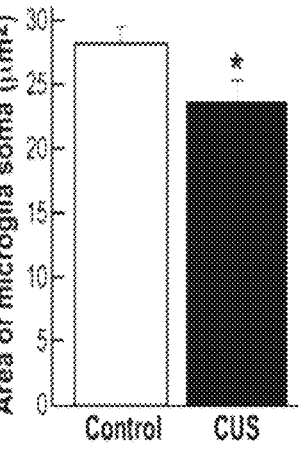
Figure 6A:
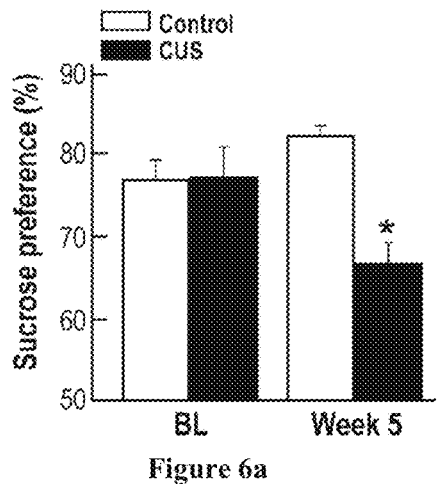
Figure 6B:
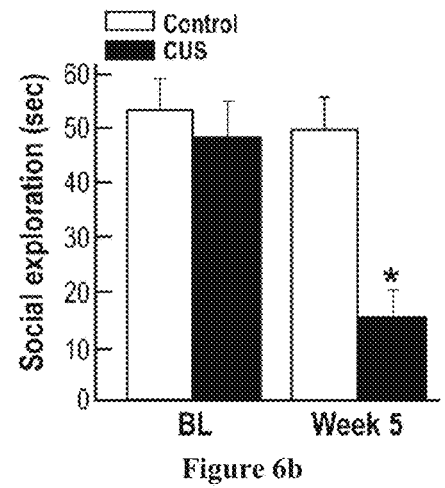
Figure 6C:
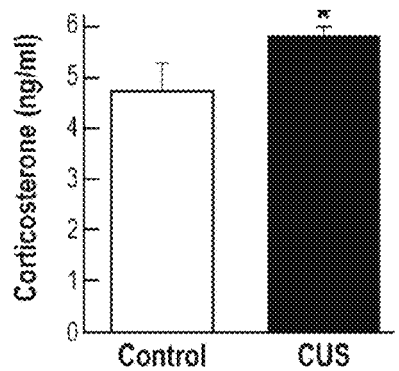
Figure 8A:
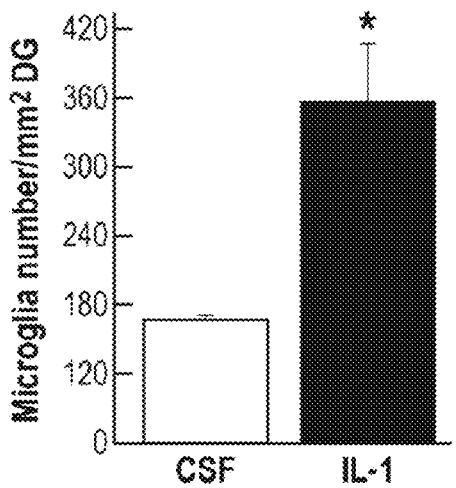
FIGS. 8a-8e. Effects of CMS in rats on depressive-like symptoms and microglia number. Effects of CMS exposure on sucrose preference (8a; $F_{5,115}=3.62$, p<0.005) and (8b) social exploration ($F_{1,23}=28.67$, p<0.0001). (8c) Effects of CMS on the number of microglia/section of the DG ($t_9=1.93$, p<0.05; n=5-6/group) and (8d) the prelimbic cortex (p>0.1). (8e) Representative pictures of CD11b staining of microglia in control and (8e) CMS-exposed rats. *p<0.05 compared with the control group.
Figure 8B:
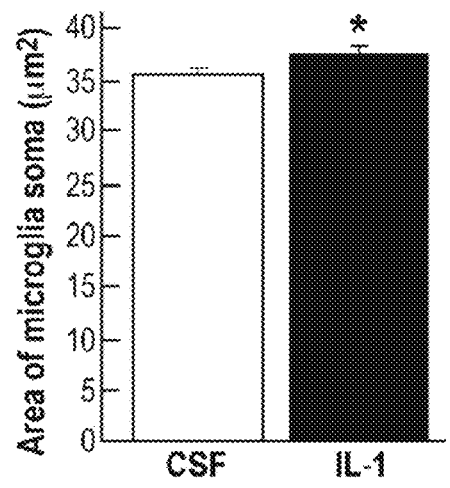
Figure 8C:
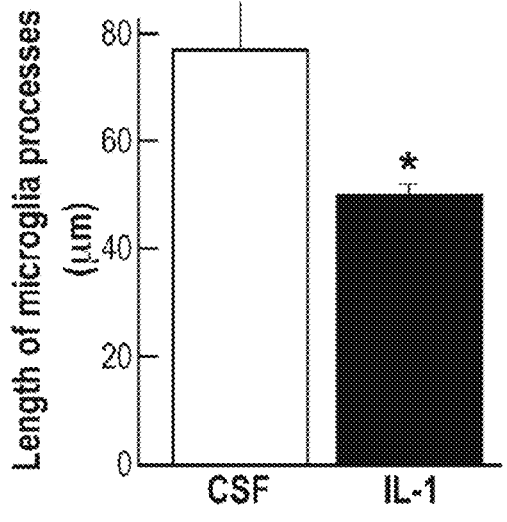
Figure 8D:
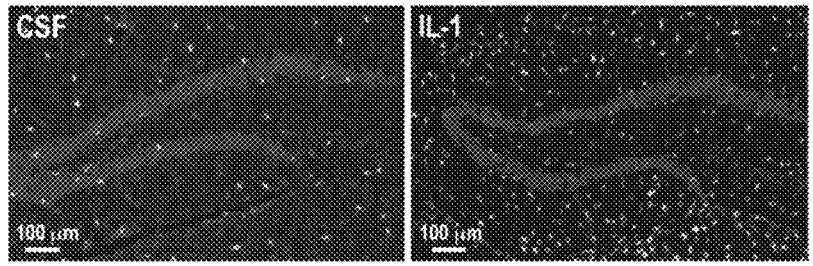
Figure 8E:
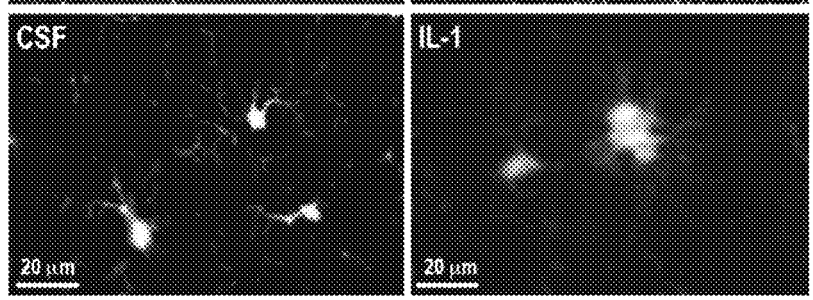

Effects of Chronic Stress on Microglia Number, Morphology and Activation Markers Expression To examine the alterations in microglial status associated with stress-induced depression-like behavior, a group of mice was exposed to 5 weeks of chronic unpredictable stress (CUS), an established paradigm for producing depressive-like behavior, and assessed their depressive symptomatology as well as their microglia number and morphology, as compared with a group of control, non-stressed mice. CUS-exposed mice displayed significant decreases in sucrose preference and social exploration, along with increased corticosterone levels (FIG. 6a-c). Surprisingly, CUS-exposed mice exhibited decreased numbers of microglia in the hippocampal dentate gyrus (DG) (FIG. 1a-c) and to a lesser extent also in the medial prefrontal cortex (PFC) (FIG. 1d), but not in the somatosensory cortex (FIG. 1e). Some microglia within the DG assumed a dystrophic morphology (FIGS. 1f-g), reflected by overall significant reductions in the length of microglial processes (FIG. 1h) and in soma area (FIG. 1i). Similar effects were obtained when microglia were stained with Iba-1, verifying that these numerical and morphological alterations did not result from down-regulation of CX3CR1 (FIGS. 6d-k). No apoptotic cells were found in either CUS-exposed or control mice following staining with either caspase-3 or TUNEL, suggesting that the microglial decline occurred at an earlier stage during the exposure to CUS.

Figure 1J:
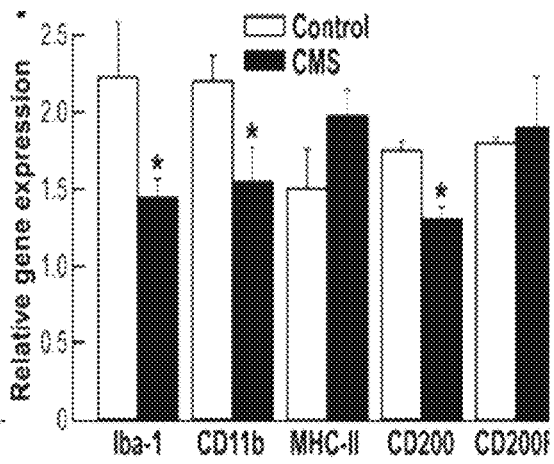

Corroborating the generality of these findings, exposure of rats to chronic mild stress (CMS) resulted in significant decreases in sucrose preference (FIG. 7), and social exploration (FIG. 7b), along with decreased microglia number in the DG (FIG. 7c) and to a lesser (non-significant) extent in the medial prefrontal cortex (FIG. 7d). In addition, CMS exposure significantly reduced the mRNA expression levels of the microglial markers CD11b and Iba-1, as well as the neuronal marker CD200, which normally keeps microglia in relative quiescence (FIG. 1j). Furthermore, in the CMS-exposed, but not in control rats, high negative correlations were obtained between the changes in sucrose preference from baseline to 5 weeks post CMS initiation and the expression of CD11b ($r=-0.771$ vs. 0.222, respectively, $p<0.05$) and Iba-1 ($r=-0.437$ vs. 0.191, respectively, not significant). That is, lower microglial marker expression was associated with greater anhedonia.

Example 2

Effects of Short-Term Exposure to US on Microglia Number, Morphology and Activation Marker Expression In contrast with the findings presented above, previous studies on the effects of stress on microglial status reported activation, rather than suppression of these cells. Because these studies employed shorter periods of stress exposure than the 5-weeks period used in the CUS model, we examined the microglial alterations induced by 1-4 days of US exposure. At day 2 following US initiation, the number of DG microglia was significantly increased (FIG. 2a), and the cells assumed an activated morphology (FIGS. 2b, 2c), characterized by increased soma area (FIG. 2d) and reduced processes length (FIG. 2e). At day 4 following US initiation, microglia number and soma size reverted whereas the processes length remained shorter (FIGS. 2a, d, e). At 24 hr following the initiation of US exposure, the mRNA expression of the microglia activation markers Iba-1 and MHC-II was significantly increased, whereas the expression of the microglial CD200 receptor (CD200R), which serves to keep microglia in relative quiescence, was significantly decreased (FIG. 2f). To determine the mechanisms underlying the initial increase and subsequent decrease in microglia number we investigated the effects of US on microglial proliferation and consequent apoptosis. Following 2 days of US exposure, but not at later time points, microglia exhibited substantial proliferation (FIG. 2g-i), whereas following 3 days of US exposure microglia exhibited a markedly increased labeling with caspase-3 (FIG. 2j-k, FIG. 9), which is critically important for microglia activation, but is also considered the "executioner of apoptosis", whose expression usually reflects a commitment to cell death. Indeed, at 4 (but not at 2) days post US-initiation, the stressed mice displayed a substantial number of TUNEL-stained apoptotic microglia (FIG. 2l-m), whereas not even a single TUNEL-stained microglia cell was encountered in control (non-stressed) mice.

Example 3

Effects of Minocycline, Imipramine and IL-1 Signaling Blockade on Stress-Induced Dynamic Microglial Alteration and Development of Depressive Symptomatology To examine the hypothesis that the initial stress-induced microglial activation is involved in the subsequent microglia decline and development of depressive behaviors, we examined the effects of pharmacological blockade of microglial activation using minocycline and genetic blockade of the microglia-stimulating cytokine interleukin (IL)-1, using mice with transgenic over-expression of brain IL-1 receptor antagonist (IL-1raTG mice). Because antidepressant drugs were previously shown to exert anti-inflammatory effects, including suppression of microglial activation, we also examined the microglial modulating effects of the tricyclic antidepressant imipramine. Minocycline administration (40 mg/kg/day via the drinking water, beginning 2 days before US initiation) completely reversed the increase in hippocampal microglia following 2 days of US exposure (FIG. 3a). Moreover, less caspase-3-labeled and TUNEL-stained apoptotic microglia were observed in US-exposed mice treated with minocycline (as compared with water only) at 3-4 days following the initiation of US exposure (FIG. 3b). Minocycline administration beginning two days before and continuing throughout the 5-weeks CUS exposure period blocked the decline in hippocampal microglia number (FIG. 3c) and completely prevented the suppressive effects of CUS on sucrose preference (FIG. 3d), with a similar trend for social exploration (FIG. 3e) and neurogenesis (FIG. 3f).

Figure 3G:
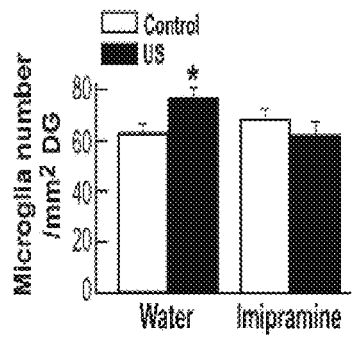
FIGS. 3a-3r. Effects of pharmacological and genetic modulation of microglial status on stress-induced depressive behavior. (3a) Effect of minocycline on the number of DG microglia following 2 days of US exposure (n=4-5/group) ($F_{1,16}$=7.45, P<0.05, for stress by treatment interaction). (3b) Effects of minocycline on the number of caspase-3 and TUNEL-stained microglia in the DG following 3-4 days of US exposure (n=4-5/group) ($t_6$=4.09 and 1.93, respectively, p<0.05). (3c) Effect of minocycline on the number of DG microglia following 5 weeks of CUS exposure (n=5-6/group) ($F_{1,17}$=9.47, P<0.05, for stress by treatment interactions). (3d) Effects of minocycline on CUS-induced reductions in sucrose preference and (3e) social exploration ($F_{1,31}$=25.389 and 3.54, P<0.0001 and P=0.07, respectively, for stress by treatment interactions). (3f) Effect of minocycline on CUS-induced reduction in neurogenesis ($F_{1,17}$=16.85 and 10.32, P<0.001 and P=0.059, for the stress and treatment effects, respectively, with no significant stress by treatment interaction). (3g) Effect of imipramine on the number of DG microglia following 2 days of US exposure (n=6-9/group) ($F_{1,24}$=7.91, P<0.01, for stress by treatment interaction). (3h) Effects of imipramine treatment throughout the CUS exposure period on CUS-induced suppression of DG microglia number, (3i) their processes length ($F_{3,12}$=9.211 and 15.50, respectively, p<0.05, for the group by treatment interactions; n=6/group), and (3j) their soma size (for which the interaction effect did not reach statistical significance). (3k) Effects of imipramine on CUS-induced reductions in sucrose preference and (3l) social exploration (F(1,20)=4.36 and 56.82, respectively, p<0.05, for group by treatment interactions; n=6/group). (3m) Effects of US on mRNA expression of IL-1-related genes in rats. At 24 hr post US initiation, hippocampal mRNA expression of IL-1ra was decreased, whereas IL-1RI expression was increased ($t_{10}$=5.12 and 3.25, p<0.01) and the expression of IL-1β and ICE was not altered; n=6/group). (3n) Effects of 2 days US exposure on DG microglia number in wild type (WT) vs. IL-1raTG mice ($F_{1,34}$=6.04, P<0.05 for stress by strain interaction; n=8-10/group). (3o) Effects of CMS in rats on mRNA expression of IL-1-related genes. CMS exposure reduced ICE expression (t9=2.21, P<0.05), but it had no effects on other IL-1-related molecules (n=5-6/group). (3p) Effects of CUS on microglia number in WT and IL-1raTG mice ($F_{1,19}$=5.11, p<0.05, n=5-6/group). (3q) Effects of CUS on sucrose preference and (3r) social exploration in WT and IL-1raTG mice ($F_{1,28}$=3.87 and 6.04, respectively, P<0.05, for stress by strain interactions; n=7-8/group). *p<0.05 compared with water drinking or WT control mice.
Figure 3H:
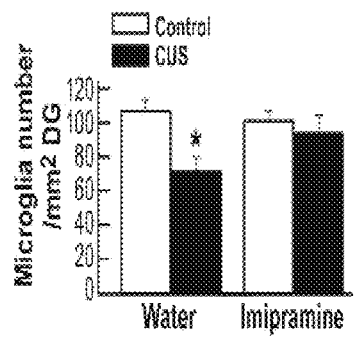
Figure 3I:
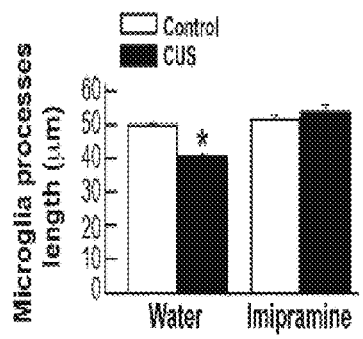
Figure 3J:
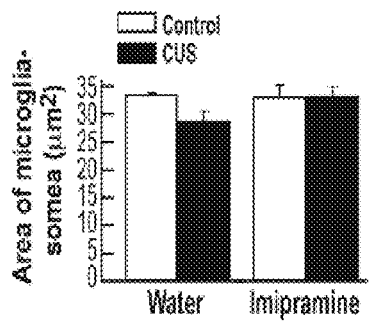
Figure 3K:
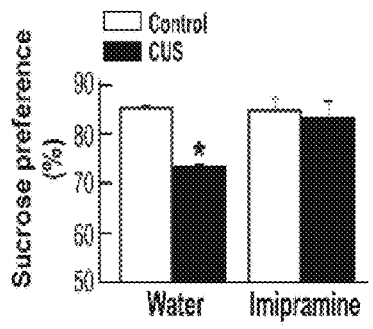
Figure 3L:
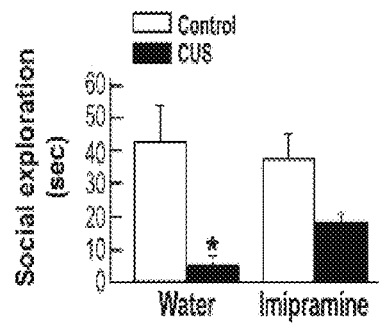

Imipramine administration (20 mg/kg/day via the drinking water, beginning 2 days before US initiation) completely reversed the increase in hippocampal microglia following 2 days of US exposure (FIG. 3g). Imipramine administration beginning two days before and continuing throughout the 5-weeks CUS exposure period blocked the CUS-induced decline in hippocampal microglia number (FIG. 3h) as well as their processes length (FIG. 3i) and soma size (FIG. 3j). The imipramine treatment also prevented the CUS-induced reductions in sucrose preference (FIG. 3k) and social exploration (FIG. 3l).

Figure 3M:
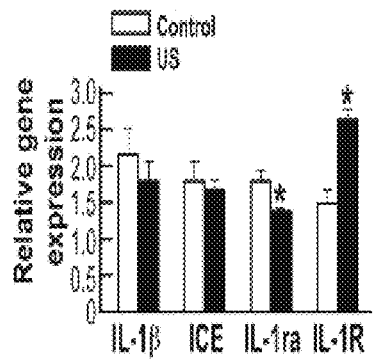
Figure 3N:
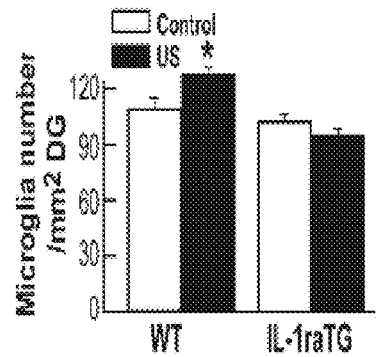
Figure 3O:
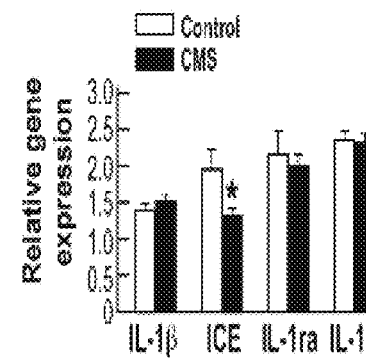
Figure 3P:
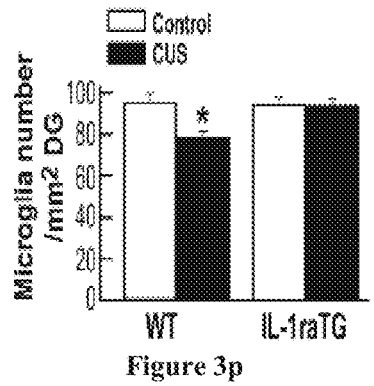
Figure 3Q:
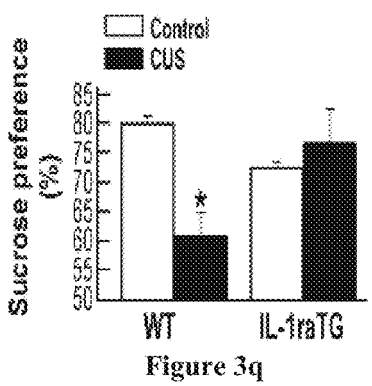
Figure 3R:
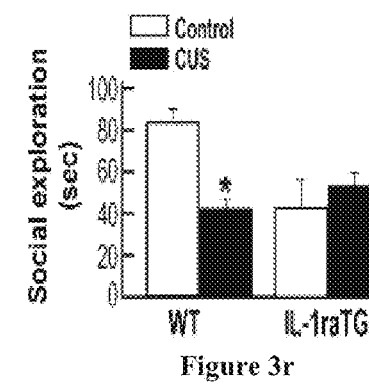

Following 24 hr of US exposure, the mRNA expression of IL-1β and IL-1 converting enzyme (ICE; the inflammasome-associated enzyme required for processing and activating IL-1β) did not change, however the expression of IL-1ra was decreased and the expression of IL-1 receptor type I (IL-1RI) was increased (FIG. 3m), suggesting an overall increase in IL-1 signaling. This increase is functionally important because after 2 days of US exposure, WT mice displayed an increase in the number of DG microglia, whereas IL-1raTG mice showed no change in microglia number (FIG. 3n). Furthermore, acute intra-hippocampal administration of IL-1β in WT mice mimicked the effects of short-term US on microglia number and morphology (FIG. 8). In contrast with the effects of short-term US, exposure to CMS in rats significantly decreased the mRNA expression of ICE, but had no effect on the expression of IL-1β, IL-1ra and IL-1R, representing an overall decreased IL-1 signaling (FIG. 3o). The impaired IL-1 signaling in IL-1raTG mice was associated with a complete blockade of the CUS-induced decrease in hippocampal microglia number (FIG. 3p), as well as the suppression of sucrose preference (FIG. 3q) and social exploration (FIG. 3r).

Example 4

Figure 4A:
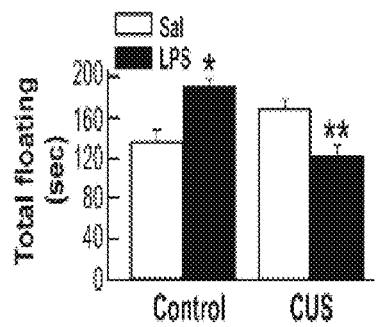
FIGS. 4a-4p. Anti-depressive effects of microglial stimulation in CUS-exposed ("depressed-like") mice. (4a) Effects of LPS in Control and CUS-exposed mice on floating time and (4b) latency to first float in the Porsolt forced swim test ($F_{1,48}$=18.73 and 13.21, P<0.001 and P<0.01, respectively, for stress by treatment interactions; n=8-12/group). (4c) Effects of LPS on DG microglia number ($F_{3,31}$=9.80, P<0.05, for the overall effect of LPS), as well as (4d) the number of BrdU-labeled DG cells ($F_{1,20}$=4.93, P<0.05, for stress by treatment interaction). (4e) Effects of M-CSF in Control and CUS-exposed mice on floating time ($F_{1,31}$=5.60, P<0.05, for stress by treatment interaction) and (4f) latency to first float (P>0.1) in the Porsolt test (n=9/group). (4g) Effects of M-CSF on sucrose preference and (4h) social exploration ($F_{1,31}$=7.75 and 5.52, P<0.01 and P<0.05, respectively, for stress by treatment by time interactions). (4i) Effects of M-CSF on DG microglia number ($F_{1,22}$=8.61, P<0.05, for the overall effect of M-CSF), as well as (4j) the number of GFP labeled microglia co-labeled for BrdU, and (4k) the number of non-microglia proliferating (BrdU-labeled) cells ($F_{1,24}$=16.06 and 8.82, respectively, P<0.01, for stress by treatment interactions). (4k) Effects of various treatments, administered to 5-weeks CUS-exposed mice over an additional two weeks CUS exposure period, on DG microglia number ($F_{4,42}$=8.61, P<0.001) (n=8-13/group), as well as on (4m) total floating time ($F_{4,49}$=8.61, P<0.05) and (4n) the latency to first float in the Porsolt forced swim test (p>0.1). (4o) Effects of various treatments on sucrose preference (($F_{4,47}$=6.76, P<0.001, for group by measurement (before vs. after treatment) interaction), and (4p) social exploration ($F_{4,48}$=4.84, P<0.05 for treatment (before vs. after treatment) effect). *p<0.05 compared with Control non-stressed mice. p<0.05 compared with CUS-exposed saline-injected mice and with LPS-injected control mice. *p<0.05 compared with CUS-exposed saline-injected mice. +p<0.05 compared with both Control non-stressed mice and with CUS-exposed mice treated with GM-CSF. ++p<0.05 compared with the corresponding Control non-stressed mice either before or after drug treatment. # p<0.05 compared with the corresponding water- or minocycline-drinking CUS-exposed mice after drug treatment. †p<0.05 compared with the corresponding "Before drug" condition.
Figure 4B:
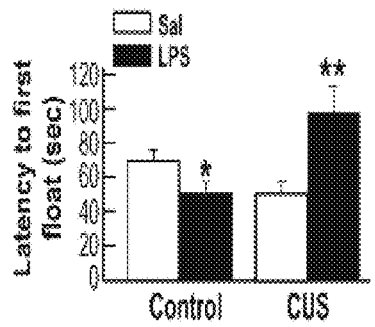
Figure 4C:
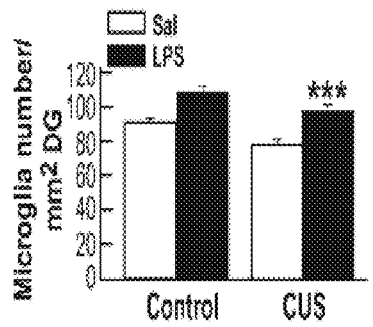
Figure 4D:
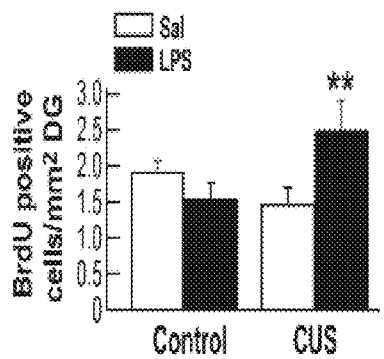

Effects of Microglia Stimulation in Chronically Stressed ("Depressed-Like") Mice on Depressive-Like Symptoms and Neurogenesis To provide direct causal evidence for the involvement of microglia depletion in CUS-induced depressive-like symptoms and suppressed neurogenesis, we examined the possible anti-depressive effects of microglia stimulation in CUS-exposed mice, using two of the most well characterized microglia activators—LPS (endotoxin) and M-CSF. In the first experiment, following verification that CUS exposure produced the expected decreases in sucrose consumption and social exploration, the control and CUS-exposed mice were acutely administrated with either LPS (100 μg/kg, i.p.) or saline. Four to five hr later, their behavior was assessed in the Porsolt forced swim test (an established test for depressive-like behavior in rodents), as well as the open field, social exploration and sucrose preference tests (the latter was conducted 24 hr post-injections). Whereas in control (non-stressed) mice LPS increased floating time (FIG. 4a) and decreased the latency to first float (FIG. 4b), in CUS-exposed mice it produced the opposite effects, completely reversing the depression/despair-like behaviors. Similarly, LPS administration reduced locomotor activity (FIG. 9a) in the open field test and the time spent in the center of the field (considered a measure of anxiety) (FIG. 9b) in control mice, whereas in CUS-exposed mice LPS increased locomotor activity and the time spent in the center of the filed, reversing the suppressive effects of CUS on these parameters. LPS administration did not significantly reverse the CUS-induced decreases in sucrose preference (FIG. 9c) and social exploration (FIG. 9d). LPS administration produced an overall increase in DG microglia number, completely normalizing the CUS-induced reduction in microglia number (FIG. 4c). Finally, whereas in control mice LPS produced a small decrease in the generation of BrdU-labeled (new) DG cells, in CUS-exposed mice it caused a dramatic increase in cell generation, completely reversing the CUS-induced suppression of this process (FIG. 4d).

Figure 4E:
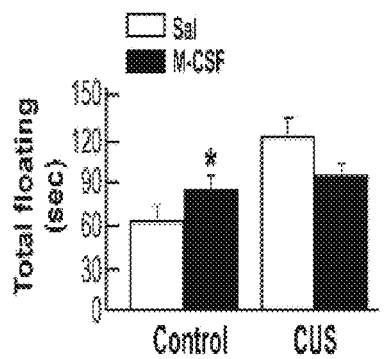
Figure 4F:
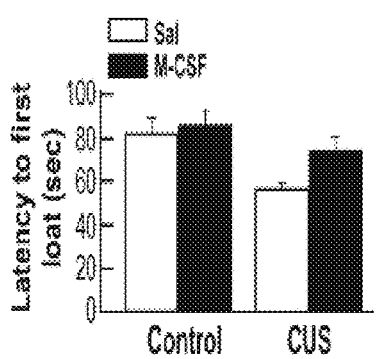
Figure 4G:
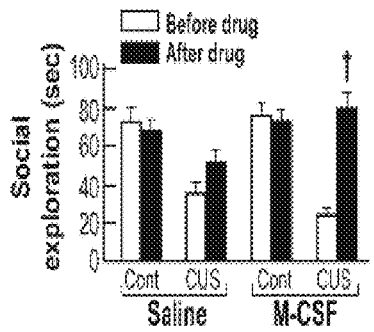
Figure 4H:
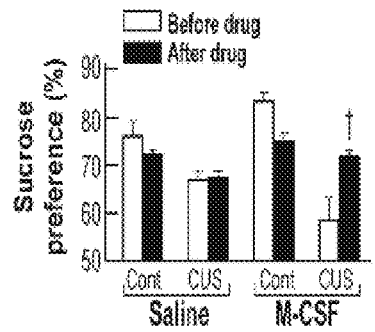
Figure 4I:
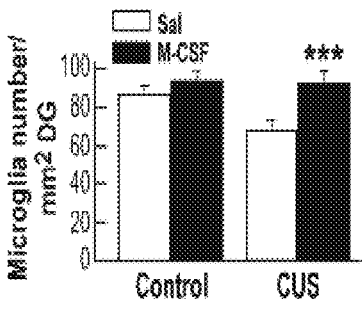
Figures 4J, 4K, 4L:
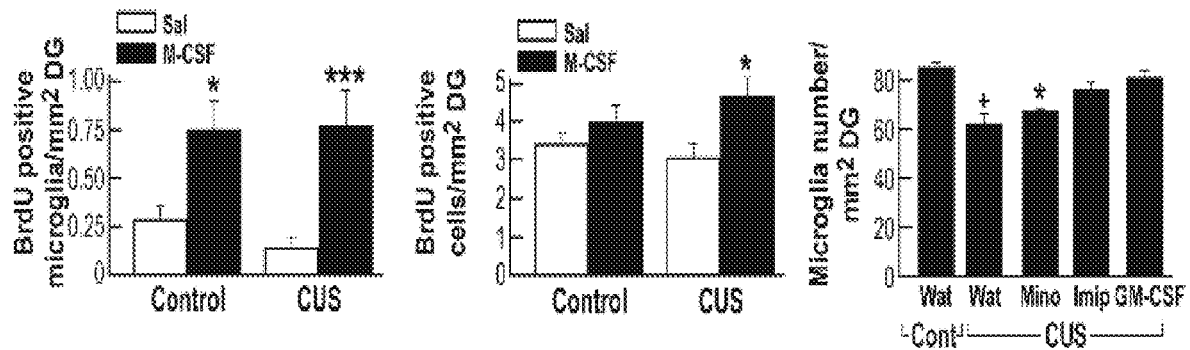

In the second experiment, following verification that CUS exposure produced the expected decreases in sucrose consumption and social exploration, the control and CUS-exposed mice were injected daily (i.p.) with either M-CSF (100 µg/kg) or saline for 5 days. Following the fifth injection, saline-treated CUS-exposed mice displayed elevated floating time in the Porsolt forced swim test and this effect was reversed by M-CSF (FIG. 4e). A similar pattern of results was obtained with respect to the latency to first float, but this finding did not reach statistical significance (FIG. 4f). Treatment with M-CSF, but not saline also completely reversed the suppressive effects of CUS on sucrose preference (FIG. 4g) and social exploration (FIG. 4h). M-CSF administration produced an overall increase in DG microglia number, completely normalizing microglia number in CUS-exposed mice (FIG. 4i), as well as an overall increase in microglia proliferation (FIG. 4j). Furthermore, CUS-exposed mice injected with M-CSF also displayed a marked increase in the generation of new (BrdU-labeled) DG cells that are not microglia (FIG. 4k).

Figures 4M, 4N:
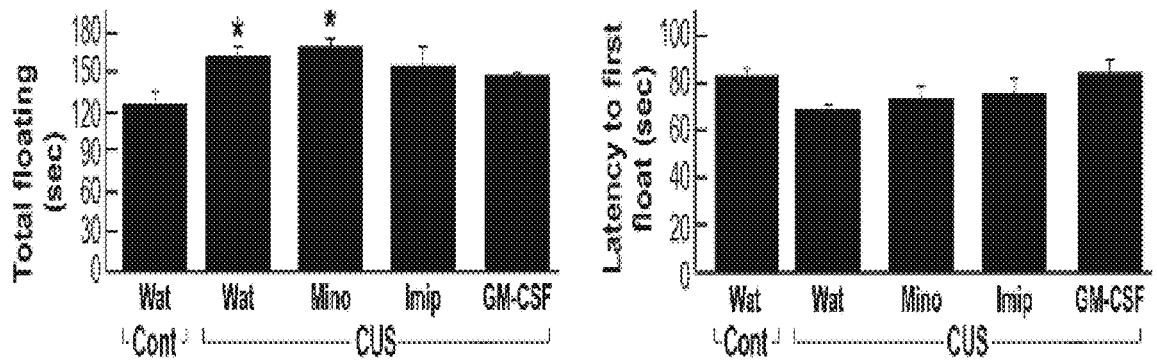
Figure 4O:
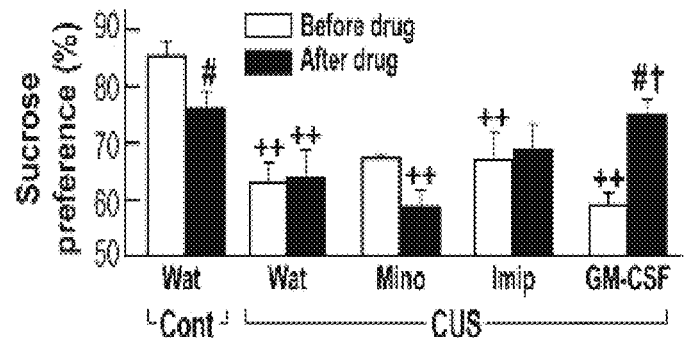
Figure 4P:
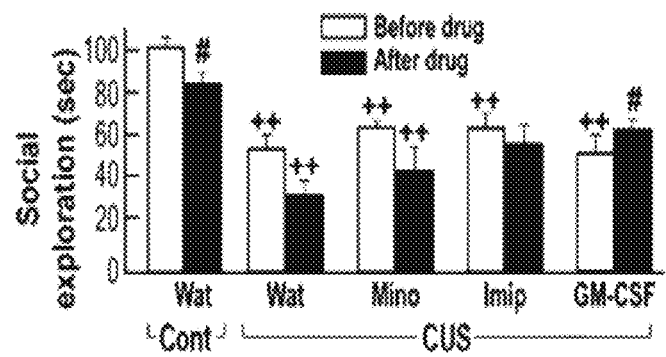

In a third experiment, we tested the effects of imipramine and minocycline (which, as shown above, produce anti-depressive effects when administered throughout the CUS exposure period) in CUS-exposed mice (i.e., when the mice already exhibited depressive-like symptoms). GM-CSF, which is known to induce microglial activation, was used as a positive control. Following verification that CUS exposure produced the expected decreases in sucrose consumption and social exploration, animals were treated with the drugs for 2 weeks (imipramine and minocycline were administered continuously via the drinking water and GM-CSF was injected i.p. 3 time/week). The various treatments produced differential effects on DG microglia number (FIG. 4l), reflected by a significant group difference. Specifically, whereas both water and minocycline-drinking CUS-exposed mice displayed significant reductions in DG microglia numbers (as compared with control non-stressed mice), imipramine-treated mice displayed no differences from any of the groups whereas GM-CSF-treated CUS-exposed mice displayed significantly greater number of microglia as compared with the control CUS-exposed mice (FIG. 4l). Water- and minocycline-drinking CUS-exposed mice displayed significantly elevated floating time in the Porsolt forced swim test, whereas imipramine and GM-CSF-treated mice showed no difference from non-stressed controls (FIG. 4m). A similar pattern of results was obtained with respect to the latency to first float (FIG. 4n). Treatment with GM-CSF, but not minocycline or imipramine, completely reversed the suppressive effects of CUS on sucrose preference (FIG. 4o). In the social exploration test, all the CUS-exposed groups displayed reduced exploration time before the treatment, and further reductions were evident during the 2-weeks drug administration period in the water-, minocycline- and imipramine-treated animals. In contrast, treatment with GM-CSF induced an elevation in the social exploration time (FIG. 4p).

The results indicate that chronic stress produces dynamic, bi-directional alterations in microglia status, including an initial phase of proliferation and activation followed by apoptosis, dystrophy and decline. The effects of chronic stress were at least partly selective to the hippocampus, suggesting that microglia decline contributes, probably along with reductions in neurogenesis, neuronal elements and astrocyte numbers, to the known decreases in the volume of this structure in depressed humans. The results further demonstrate that stimulation of microglia in CUS-exposed mice reversed their depressive-like neuro-behavioral symptomatology, providing the first direct causal evidence that disturbances in microglial functioning has an etiological role in psychopathology, in general, and in major depression, in particular (FIG. 5).

The model suggests that depression cannot be treated unitarily. Indeed, effective anti-depressive procedures should take the inflammatory/microglial status into account and depending on whether these cells are activated or suppressed, either microglia suppressive agents (e.g., minocycline, IL-1 signaling blockers) or microglia activating drugs (e.g., M-CSF, GM-CSF) should be employed.

The finding that a relatively short-term exposure to unpredictable stress (US) results in microglia proliferation and activation is consistent with previous studies, demonstrating that exposure to acute tail-shock stress results in hippocampal microglia activation and repeated daily restraint for 4-21 days produces increased microglial number and activated morphology in hippocampus and prefrontal cortex. The results further suggest that the US-induced microglia proliferation and activation depend on signaling via the IL-1 receptor, as they did not occur in mice with transgenic over-expression of IL-1ra. Furthermore, the results suggest that the initial US-induced microglia activation was responsible for the subsequent microglial apoptosis and decline, as well as the development of depressive symptomatology and suppressed neurogenesis, because all of these effects were also prevented by minocycline or IL-1ra over-expression, whereas minocycline administration to mice with established CUS-induced depressive-like behavior had no beneficial effect. Similar to the effects of minocycline, the anti-depressive effects of imipramine also seem to depend at least partly on suppression of the initial microglial activation and the subsequent microglial decline, consistently with the known acute anti-inflammatory effects of antidepressant drugs, because imipramine administration to mice with established CUS-induced depressive-like behavior produced minimal beneficial effects.

The finding that stress-induced proliferation and activation was followed by microglial apoptosis corroborates the results of a previous study demonstrating the same phenomenon using flow cytometric methodology, although no apoptosis was found in other studies on the effects of repeated restraint stress on microglial status. Interestingly, the apoptosis-related molecule caspase-3, which in the present study was found to be elevated three days post-US initiation, has recently been shown to be critically involved in regulating microglia activation (consistently with other indices of microglia activation at this time, see FIG. 2). Caspase-3 elevation was shown to lead to microglial apoptosis in some studies, but not in others. Similar inconsistent findings also characterize the effects of various chronic stress procedures on inflammatory cytokines, with some studies reporting elevated brain cytokine levels, other studies reporting deceased levels and yet additional studies reporting no effects of chronic stressors on inflammatory cytokines levels. Together with the results of the present study, these findings suggest that various stress procedures produce either activation or decline of microglia number and functioning, as well as dynamic transitions between activation and decline, possibly depending on various parameters of the stress paradigm (e.g., type, severity, duration/chronicity) and other variables such as the subjects' genetics and environmental conditions. Based on the finding that the microglia decline occurred at a later phase of stress exposure than did microglia activation, it may be suggested that in human microglia decline accounts for depression associated with chronic stressors such as poverty, medical disabilities, or lasting marital discord, which are indeed associated more strongly with depressive symptomatology than are acute stressors such as specific negative life events.

Over the last decade it has become evident that microglia are not merely idle cells, waiting to be activated by injury or infection, but rather are active and motile in their "quiescent" state, interacting with neurons and other cellular components, and participating in physiological processes such as synaptic formation and pruning. These findings are consistent with the emerging notion that immune-like processes play an important modulatory role in brain and behavioral functioning. However, despite the evolving literature on the physiological role of "quiescent" microglia, there is almost no data on their direct contribution to the regulation of behavioral/psychological processes.

The findings of the present study provide one of the first direct demonstrations that suppression of microglia activation status and reduction in their number can produce detrimental neuro-behavioral effects, in contrast with previous neurological and psychiatric literature, which implicated only microglial activation in neuro- and psychopathology.

Administration of LPS to CUS-exposed mice, which increased hippocampal microglia number to normal levels, partially reversed the depressive-like behavioral symptoms and suppressed neurogenesis. Interestingly, in accordance with previous studies LPS produced the opposite effects, i.e., depressive like behavior and suppressed neurogenesis in non-stressed mice, emphasizing the importance of studying the properties of anti-depressive procedures using a chronic model of depression. The fact that LPS only partially reversed the CUS-induced depressive-like effects, despite completely reversing the effects of CUS on microglia and neurogenesis, may be related to the acute nature of this experiment, considering that LPS was injected only once and behavioral measurements were taken several hours before the animals were sacrificed (allowing more time for LPS to produce its effects on microglia and neurogenesis). In any case, the partial anti-depressive effects of LPS in CUS-exposed mice corroborate and explain the findings of a previous clinical study demonstrating a beneficial, anti-depressive effect of LPS in severely depressed patients. M-CSF can be more translationally relevant than LPS because it did not cause depressive symptoms in non-stressed mice, and it completely reversed the depressive symptoms after a few days of treatment. GM-CSF (also termed sargramostim) may be also translationally relevant because it has been marketed under the trade names LEUKINE® (Genzyme) and LEUCOMAX® (Novartis) for more than two decades, mainly for replenishment of white blood cells following chemotherapy, acceleration of white blood cell recovery following autologous bone marrow transplantation. Thus, M-CSF, its derivatives and related molecules (e.g., IL-34), as well as GM-CSF and other microglia stimulators can serve as fast-acting anti-depressants, specifically in patients with major depression and stress-related disorders who exhibit normal or low levels of inflammatory markers.

Example 5

Blockade of CX3CR1 Signaling Induces Microglial Proliferation and Activation

To demonstrate that CX3CR1 blockade can serve as a microglial stimulating procedure, the inventors used two approaches. In the first approach the inventors compared the number and morphology of microglia between mice with genetic deletion of CX3CR1 ($CX3CR1^{-/-}$ mice) and controls. Compared with both their WT controls (C57BL/6) and with mice heterozygous for the CX3CR1 deletion (i.e., $CX3CR1^{+/-}$), mice homozygous for the CX3CR1 deletion ($CX3CR1^{-/-}$ mice) displayed elevated number of DG microglia ($p<0.05$) (FIG. 11a). The $CX3CR1^{-/-}$ mice also displayed a larger soma area, compared with the WT mice ($p<0.05$) (FIG. 11b). Furthermore, qPCR analysis of mRNA expression demonstrated increased levels of the microglial marker P2Y12 ($p<0.05$) (FIG. 11c). These findings are exemplified by representative pictures of the hippocampal DG of a WT mouse (11d) and a $CX3CR1^{-/-}$ mouse (11e), depicting IBA-1 labeled microglia (green) along with staining of all nuclei (DAPI=blue). It should be noted that elevated microglial numbers, enlargement of their soma area, and increased expression of P2Y12, are usually indicative of an activated phenotype. To examine the effects of pharmacological blockade of CX3CR1 signaling, the inventors administered a CX3CR1 monoclonal antibody directly into the brain (via an intracerebroventricular (i.c.v.) cannula). Following two weeks of administration, the number of hippocampal microglia in the antibody-administered mice was significantly greater than in vehicle-administered mice ($p<0.05$) (FIG. 12).

Example 6

Blockade of CX3CR1 Signaling Induces Resilience to Stress-Induced Depression

Figure 13A:
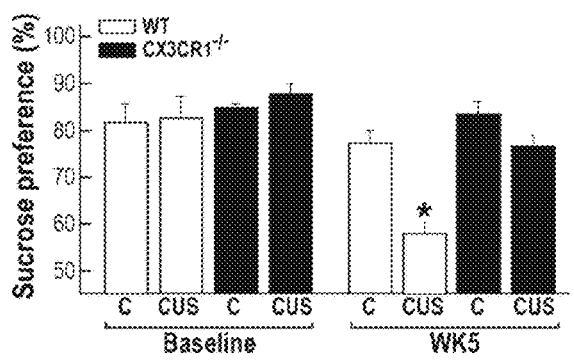
FIGS. 13a-13c. Genetic blockade of CX3CR1 signaling in CX3CR1$^{-/-}$ mice produces stress resilience and anti-depressant effects in the chronic unpredictable stress (CUS) model of depression. (13a) Following exposure to 5 weeks of CUS, WT mice showed a dramatic reduction in sucrose preference (reflective of anhedonia—a core symptom of depression). This reduction was completely blocked by the CX3CR1 deletion in CX3CR1$^{-/-}$ mice. These findings were reflected by a significant three-way interaction between time (before and after the CUS exposure)×stress (CUS vs. non-stressed control (C))×genotype (CX3CR1$^{-/-}$ vs. WT) (F1, 34=4.43, P<0.043) (n=8-10/group). Post hoc analysis revealed that sucrose preference in the CUS-exposed WT mice was significantly lower than the preference in all other groups as well as the preference of this group during baseline. (13b) Following exposure to 5 weeks of CUS, WT mice, showed a dramatic impairment in novel object recognition memory. This impairment was completely blocked by the CX3CR1 deletion in CX3CR1$^{-/-}$ mice. Three-Way ANOVA with time as a repeated measure revealed a significant effect of time (representing the object recognition (OR) memory during the test) (F1,35=43, p<0.001) (n=8-10/group). Although the 3-way interaction did to reach statistical significance, post hoc analysis revealed significant differences between novel OR and baseline for non-stressed WT and CX3CR1$^{-/-}$ mice, as well as for CUS-exposed CX3CR1$^{-/-}$ mice, but not for CUS-exposed WT mice. Furthermore, OR memory of CUS-exposed WT mice was significantly different from OR memory of non-stressed WT and CX3CR1$^{-/-}$ mice, and CUS-exposed CX3CR1$^{-/-}$ mice (13c).
Figure 13B:
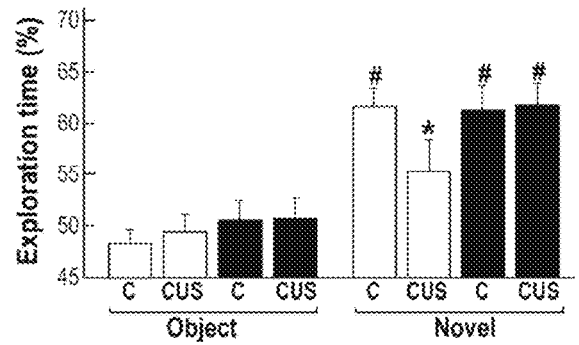
Figure 13C:
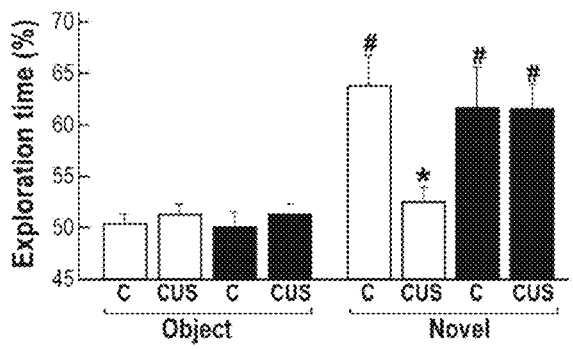

To examine the possibility that CX3CR1 blockade can serve as an anti-depressive procedure, the inventors examined the effects of choric unpredictable stress (CUS) on anhedonia (a core symptom of depression), using the sucrose preference test, in $CX3CR1^{-/-}$ and WT control mice. In addition, the inventors used the object recognition test as a measure of cognitive functioning, which is also often impaired in depression. CUS-exposed WT mice displayed reduced sucrose preference, compared with their own baseline and with all other groups during the testing period ($p<0.05$) (FIG. 13a). In contrast, $CX3CR1^{-/-}$ mice showed no significant CUS-induced reduction in sucrose preference. Furthermore, CUS-exposed WT mice also showed a significant impairment in the novel object recognition memory test ($p<0.05$), whereas $CX3CR1^{-/-}$ displayed no memory decline following CUS exposure (FIGS. 13b and 13c).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method for treating or attenuating a major depressive disorder (MDD) in a subject having plasma C-reactive protein (CRP) levels lower than 3 mg/L, the method comprising administering to the subject a pharmaceutical composition comprising a therapeutically effective amount of a chemokine C-X3-C motif ligand receptor 1 (CX3CR1) antagonist and at least one pharmaceutically acceptable carrier or diluent, wherein said CX3CR1 antagonist is an antibody.

2. The method of claim 1, further comprising the step of detecting an inflammatory state of said subject by determining the plasma level of CRP, wherein a level of less than 3 mg/L CRP indicates the subject has an inflammatory state suitable for treatment by the CXC3R1 antagonist.

3. The method of claim 1, further comprising the step of detecting an inflammatory state of said subject by determining any one of: (i) at least one inflammatory marker selected from IL-6 and TNFα, and (ii) Erythrocyte Sedimentation Rate (ESR), wherein a level of (i) less than 2.0 pg/ml IL-6, less than 3.8 pg/ml TNFα, or (ii) an ESR level of less than 6.3 mm/h, indicates the subject has an inflammatory state suitable for treatment by the CX3CR1 antagonist.

* * * * *

SEQUENCE LISTING

<160> NUMBER OF SEQ ID NOS: 27

<210> SEQ ID NO 1
<211> LENGTH: 554
<212> TYPE: PRT
<213> ORGANISM: Homo sapiens

<400> SEQUENCE: 1

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
        355                 360                 365
```

Arg Val Gly Pro Val Arg Pro Thr Gly Gln Asp Trp Asn His Thr Pro
    370             375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
            420                 425                 430

Ser Val Leu Pro Leu Gly Glu Leu Gly Arg Arg Ser Thr Arg Asp
            435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
                485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
            515                 520                 525

Gln Arg Ala Asp Ser Pro Leu Glu Gln Pro Glu Gly Ser Pro Leu Thr
530                 535                 540

Gln Asp Asp Arg Gln Val Glu Leu Pro Val
545                 550

<210> SEQ ID NO 2
<211> LENGTH: 438
<212> TYPE: PRT
<213> ORGANISM: Homo sapiens

<400> SEQUENCE: 2

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

```
Tyr Pro Lys Ala Ile Pro Ser Ser Asp Pro Ala Ser Val Ser Pro His
            195                 200                 205

Gln Pro Leu Ala Pro Ser Met Ala Pro Val Ala Gly Leu Thr Trp Glu
            210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
            290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly His Glu Arg Gln
            355                 360                 365

Ser Glu Gly Ser Phe Ser Pro Gln Leu Gln Glu Ser Val Phe His Leu
            370                 375                 380

Leu Val Pro Ser Val Ile Leu Val Leu Leu Ala Val Gly Gly Leu Leu
385                 390                 395                 400

Phe Tyr Arg Trp Arg Arg Arg Ser His Gln Glu Pro Gln Arg Ala Asp
                405                 410                 415

Ser Pro Leu Glu Gln Pro Glu Gly Ser Pro Leu Thr Gln Asp Asp Arg
            420                 425                 430

Gln Val Glu Leu Pro Val
            435

<210> SEQ ID NO 3
<211> LENGTH: 256
<212> TYPE: PRT
<213> ORGANISM: Homo sapiens

<400> SEQUENCE: 3

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65              70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
```

```
                115              120              125
Glu His Asp Lys Ala Cys Val Arg Thr Phe Tyr Glu Thr Pro Leu Gln
130                  135                  140

Leu Leu Glu Lys Val Lys Asn Val Phe Asn Glu Thr Lys Asn Leu Leu
145                  150                  155                  160

Asp Lys Asp Trp Asn Ile Phe Ser Lys Asn Cys Asn Asn Ser Phe Ala
                 165                  170                  175

Glu Cys Ser Ser Gln Gly His Glu Arg Gln Ser Glu Gly Ser Phe Ser
                 180                  185                  190

Pro Gln Leu Gln Glu Ser Val Phe His Leu Leu Val Pro Ser Val Ile
             195                  200                  205

Leu Val Leu Leu Ala Val Gly Gly Leu Leu Phe Tyr Arg Trp Arg Arg
         210                  215                  220

Arg Ser His Gln Glu Pro Gln Arg Ala Asp Ser Pro Leu Glu Gln Pro
225                  230                  235                  240

Glu Gly Ser Pro Leu Thr Gln Asp Asp Arg Gln Val Glu Leu Pro Val
                 245                  250                  255

<210> SEQ ID NO 4
<211> LENGTH: 144
<212> TYPE: PRT
<213> ORGANISM: Homo sapiens

<400> SEQUENCE: 4

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 5
<211> LENGTH: 242
<212> TYPE: PRT
<213> ORGANISM: Homo sapiens

<400> SEQUENCE: 5

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
                20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
```

```
                50                  55                  60
Ser Val Pro Tyr Glu Gly Val Phe Arg Ile Ala Asn Val Thr Arg Leu
 65                  70                  75                  80

Gln Arg Ala Gln Val Ser Glu Arg Glu Leu Arg Tyr Leu Trp Val Leu
                 85                  90                  95

Val Ser Leu Ser Ala Thr Glu Ser Val Gln Asp Val Leu Leu Glu Gly
                100                 105                 110

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
        130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro
```

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
ggcaatggag atatcgatat                                              20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
agaatcattc tcaagatggc                                              20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
ctggtacatc gagacttctc                                              20

<210> SEQ ID NO 9
<211> LENGTH: 20
<212> TYPE: DNA
<213> ORGANISM: Artificial
<220> FEATURE:

<223> OTHER INFORMATION: Primer

<400> SEQUENCE: 9
ttggtctctg tctgagcctt                                          20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
agcactggga gtttgaagag                                          20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
aagccatcac ctcctggtat                                          20

<210> SEQ ID NO 12
<211> LENGTH: 19
<212> TYPE: DNA
<213> ORGANISM: Artificial
<220> FEATURE:
<223> OTHER INFORMATION: Primer

<400> SEQUENCE: 12
tgttccgctg attgttggc                                           19

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
atggacacat tacggttgcc                                          20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14 tagaggggt gaccaattat                                           20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
tacattttct gcagccactg                                          20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
ccttgtgcaa gtgtctgaag                                              20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
gggcttggaa gcaatcctta                                              20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
atgccgtgga gagaaacaag                                              20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
ccaggacaca ttatctggtg                                              20

<210> SEQ ID NO 20
<211> LENGTH: 19
<212> TYPE: DNA
<213> ORGANISM: Artificial
<220> FEATURE:
<223> OTHER INFORMATION: Primer

<400> SEQUENCE: 20
gtctggagat gacaccaag                                               19

<210> SEQ ID NO 21
<211> LENGTH: 19
<212> TYPE: DNA
<213> ORGANISM: Artificial
<220> FEATURE:
<223> OTHER INFORMATION: Primer

<400> SEQUENCE: 21
tcggagcgga tgaaggtaa                                               19

<210> SEQ ID NO 22
<211> LENGTH: 20
<212> TYPE: DNA
<213> ORGANISM: Artificial
<220> FEATURE:
<223> OTHER INFORMATION: Primer

```
-continued

<400> SEQUENCE: 22
acccagttcc tgacttcaag                                                        20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
agtccctgta ccaaagcact                                                        20

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
tctccctcac aatttcc                                                           17

<210> SEQ ID NO 25
<211> LENGTH: 16
<212> TYPE: DNA
<213> ORGANISM: Artificial Sequence
<220> FEATURE:
<223> OTHER INFORMATION: Primer

<400> SEQUENCE: 25
gggtgcagcg aacttt                                                            16

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ctgggacaaa caagaagaaa gg                                                     22

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ccttggagca gtctggatat t                                                      21
```